United States Patent
Kabasawa

(10) Patent No.: US 8,285,360 B2
(45) Date of Patent: Oct. 9, 2012

(54) BLOOD FLOW DYNAMIC ANALYSIS APPARATUS, MAGNETIC RESONANCE IMAGING SYSTEM AND PROGRAM

(75) Inventor: Hiroyuki Kabasawa, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 330 days.

(21) Appl. No.: 12/683,991

(22) Filed: Jan. 7, 2010

(65) Prior Publication Data
US 2010/0174174 A1    Jul. 8, 2010

(30) Foreign Application Priority Data
Jan. 8, 2009    (JP) ................................ 2009-002133

(51) Int. Cl.
*A61B 5/00*    (2006.01)
*A61B 5/055*    (2006.01)

(52) U.S. Cl. ........ 600/419; 600/420; 600/431; 382/128; 382/131

(58) Field of Classification Search .................. 600/407, 600/410, 419, 420, 431; 382/128, 131
See application file for complete search history.

(56) References Cited

U.S. PATENT DOCUMENTS

| | | | | |
|---|---|---|---|---|
| 4,688,175 | A | * | 8/1987 | Kaneko et al. ................. 600/406 |
| 5,377,679 | A | | 1/1995 | Machida et al. |
| 6,275,721 | B1 | * | 8/2001 | Darrow et al. ................. 600/410 |
| 7,853,309 | B2 | * | 12/2010 | Ichihara et al. ............... 600/425 |
| 2007/0276223 | A1 | * | 11/2007 | De Bliek ........................ 600/410 |

FOREIGN PATENT DOCUMENTS

JP    2000-163561    6/2000

* cited by examiner

*Primary Examiner* — Ruth S Smith
(74) *Attorney, Agent, or Firm* — Armstrong Teasdale LLP

(57) ABSTRACT

A blood flow dynamic analysis apparatus for analyzing the dynamic state of a blood flow of a subject using data about a plurality of frame images acquired from the subject with a contrast agent injected therein, includes a map creation device for creating maps each indicative of a characteristic amount related to the dynamic state of the contrast agent or the blood flow, based on the data about the frame images, an unaffected side detection device for detecting an unaffected side of the subject from within each of the maps, and a display condition determination device for determining a display condition used when each of the maps is displayed, based on pixel values of pixels existing in the unaffected side in the map.

19 Claims, 29 Drawing Sheets

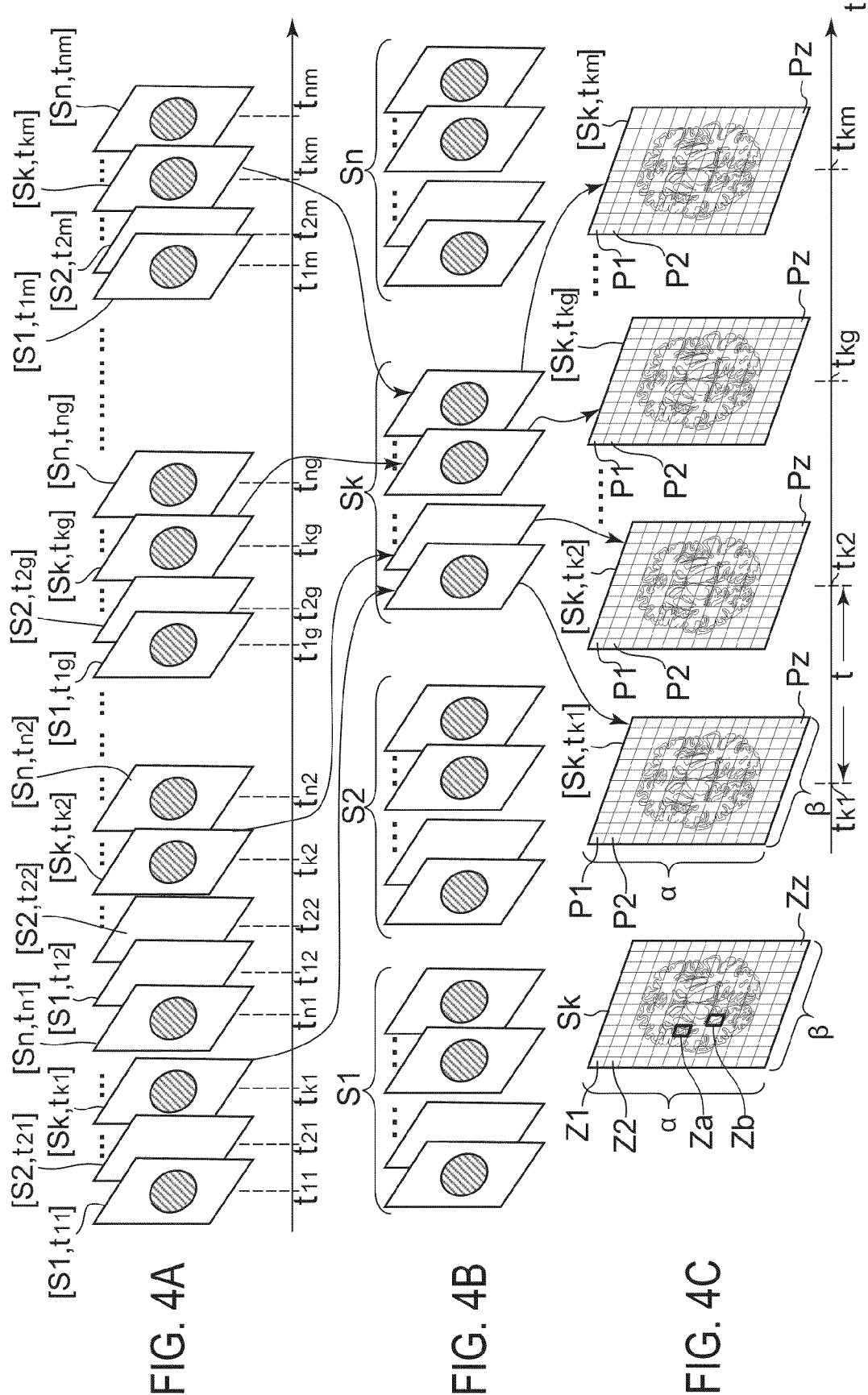

FIG. 6    FRAME IMAGE [Sk,tkg]
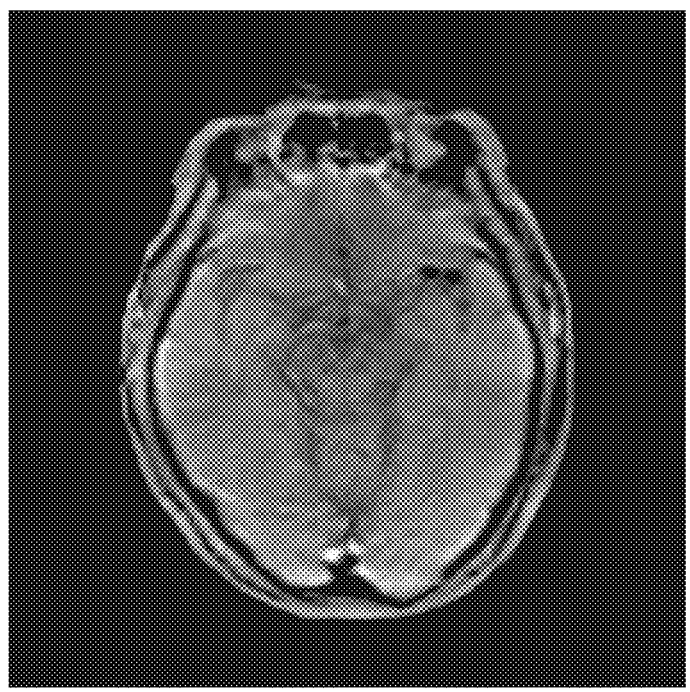
FIG. 7    FRAME IMAGE [Sk,tkg]

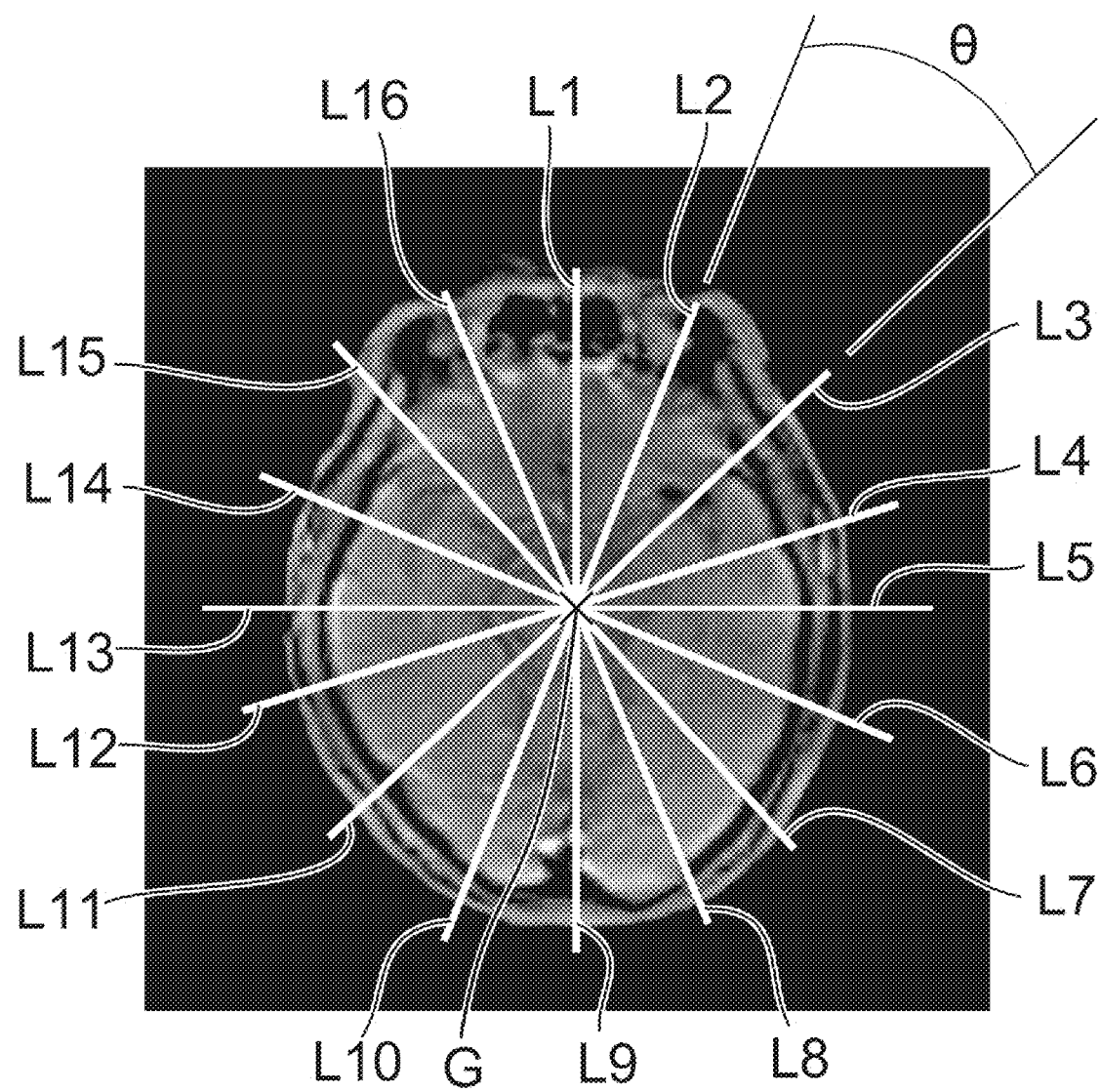

FIG. 12

| LINE | PIXEL | NUMBER OF PIXELS (PCS) |
|---|---|---|
| L1 | P1,P2,..., Pa | N1 |
| L2 | P1,P2,..., Pb | N2 |
| L3 | P1,........, Pc | N3 |
| L4 | P1,........, Pd | N4 |
| L5 | P1,........, Pe | N5 |
| L6 | P1,........, Pf | N6 |
| L7 | P1,........, Pg | N7 |
| L8 | P1,........, Ph | N8 |
| L9 | P1,........, Pi | N9 |
| L10 | P1,........, Pj | N10 |
| L11 | P1,........, Pk | N11 |
| L12 | P1,........, Pl | N12 |
| L13 | P1,........, Pm | N13 |
| L14 | P1,........, Pn | N14 |
| L15 | P1,........, Po | N15 |
| L16 | P1,........, Pq | N16 |

FIG. 13

| LINE | PIXEL | NUMBER OF PIXELS (PCS) | AVERAGE VALUE OF PIXEL VALUES |
|---|---|---|---|
| L1 | P1,P2,..., Pa | N1 | V1 |
| L2 | P1,P2,..., Pb | N2 | V2 |
| L3 | P1,........, Pc | N3 | V3 |
| L4 | P1,........, Pd | N4 | V4 |
| L5 | P1,........, Pe | N5 | V5 |
| L6 | P1,........, Pf | N6 | V6 |
| L7 | P1,........, Pg | N7 | V7 |
| L8 | P1,........, Ph | N8 | V8 |
| L9 | P1,........, Pi | N9 | V9 |
| L10 | P1,........, Pj | N10 | V10 |
| L11 | P1,........, Pk | N11 | V11 |
| L12 | P1,........, Pl | N12 | V12 |
| L13 | P1,........, Pm | N13 | V13 |
| L14 | P1,........, Pn | N14 | V14 |
| L15 | P1,........, Po | N15 | V15 |
| L16 | P1,........, Pq | N16 | V16 |

FIG. 20

| SLICE | MAP | UNAFFECTED SIDE AVERAGE VALUE U |
|---|---|---|
| S1 | CBV | $U_{CBV1}$ |
|  | CBF | $U_{CBF1}$ |
|  | MTT | $U_{MTT1}$ |
|  | BAT | $U_{BAT1}$ |
|  | TTP | $U_{TTP1}$ |
| ⋮ | ⋮ | ⋮ |
| Sk | CBV | $U_{CBVk}$ |
|  | CBF | $U_{CBFk}$ |
|  | MTT | $U_{MTTk}$ |
|  | BAT | $U_{BATk}$ |
|  | TTP | $U_{TTPk}$ |
| ⋮ | ⋮ | ⋮ |

MTT MAP OF SLICE Sk

BLOOD FLOW DYNAMIC ANALYSIS APPARATUS, MAGNETIC RESONANCE IMAGING SYSTEM AND PROGRAM

CROSS REFERENCE TO RELATED APPLICATIONS

This application claims the benefit of Japanese Patent Application No. 2009-002133 filed Jan. 8, 2009, which is hereby incorporated by reference in its entirety.

BACKGROUND OF THE INVENTION

The embodiments described herein relate to a blood flow dynamic analysis apparatus for analyzing the dynamic state of a blood flow of a subject, a magnetic resonance imaging system having the blood flow dynamic analysis apparatus, and a program for analyzing the dynamic state of the blood flow of the subject.

In order to diagnose using each MR image whether a lesion is developing in the head of a subject, it must be able to visually distinguish between an affected or lesion side and an unaffected side (side or portion free of the existence of an anomaly such as a lesion) in the head within the MR image. In order to display the MR image in such a manner that the lesion side and the unaffected side can be visually distinguished from each other, there is a need to set a window level and a window width to optimum values respectively. There has thus been known a method capable of adjusting a window level and a window width by an operator (refer to a Japanese Unexamined Patent Publication No. 2000-163561).

The method described above is however accompanied by a problem in that since the window level and the window width are manually set, it takes time to display a perfusion image suitable for diagnosis of the affected or lesion side.

BRIEF DESCRIPTION OF THE INVENTION

Embodiments of the invention provide a blood flow dynamic analysis apparatus for analyzing the dynamic state of a blood flow of a subject using data about a plurality of frame images acquired from the subject with a contrast agent injected therein, including: a map creation device for creating maps each indicative of a characteristic amount related to the dynamic state of the contrast agent or the blood flow, based on the data about the frame images; an unaffected side detection device for detecting an unaffected side of the subject from within each of the maps; and a display condition determination device for determining a display condition used when each of the maps is displayed, based on pixel values of pixels existing in the unaffected side in the map.

Moreover, embodiments provide a program that causes a blood flow dynamic analysis apparatus for analyzing the dynamic state of a blood flow of a subject using data about a plurality of frame images acquired from the subject with a contrast agent injected therein, to function as: a map creation device for creating maps each indicative of a characteristic amount related to the dynamic state of the contrast agent or the blood flow, based on the data about the frame images; an unaffected side detection device for detecting an unaffected side of the subject from within each of the maps; and a display condition determination device for determining a display condition used when each of the maps is displayed, based on pixel values of pixels existing in the unaffected side in the map.

In some embodiments, each line existing in an unaffected side is detected from a plurality of lines overlaid on each of maps indicative of characteristic amounts. A condition for displaying each map is determined based on the average value of pixel values of pixels overlaid on the detected line. Thus, when a lesion exists in a subject's imaging range, an unaffected side and an affected or lesion side can be represented in different shades of gray. An operator is therefore able to specify the lesion side easily.

Further embodiments of the present invention will be apparent from the following description as illustrated in the accompanying drawings.

BRIEF DESCRIPTION OF THE DRAWINGS

FIGS. 4A, 4B, and 4C are conceptual diagrams showing frame images obtained from slices S1 through Sn.

FIG. 6 is a schematic diagram of a selected frame image.

FIG. 7 is a diagram showing the position of calculated center of gravity G.

FIG. 8 is a diagram illustrating a frame image [Sk, tkg] formed with a plurality of lines.

FIG. 12 is a table in which pixels determined to be overlaid on the lines L1 through L16 are represented every line.

FIG. 13 is a table showing average values of pixel values calculated every line.

FIG. 20 is a table showing unaffected side average values U calculated with respect to all maps of slices S1 through Sn.

DETAILED DESCRIPTION OF THE INVENTION

(1) First Embodiment

Figure 1:
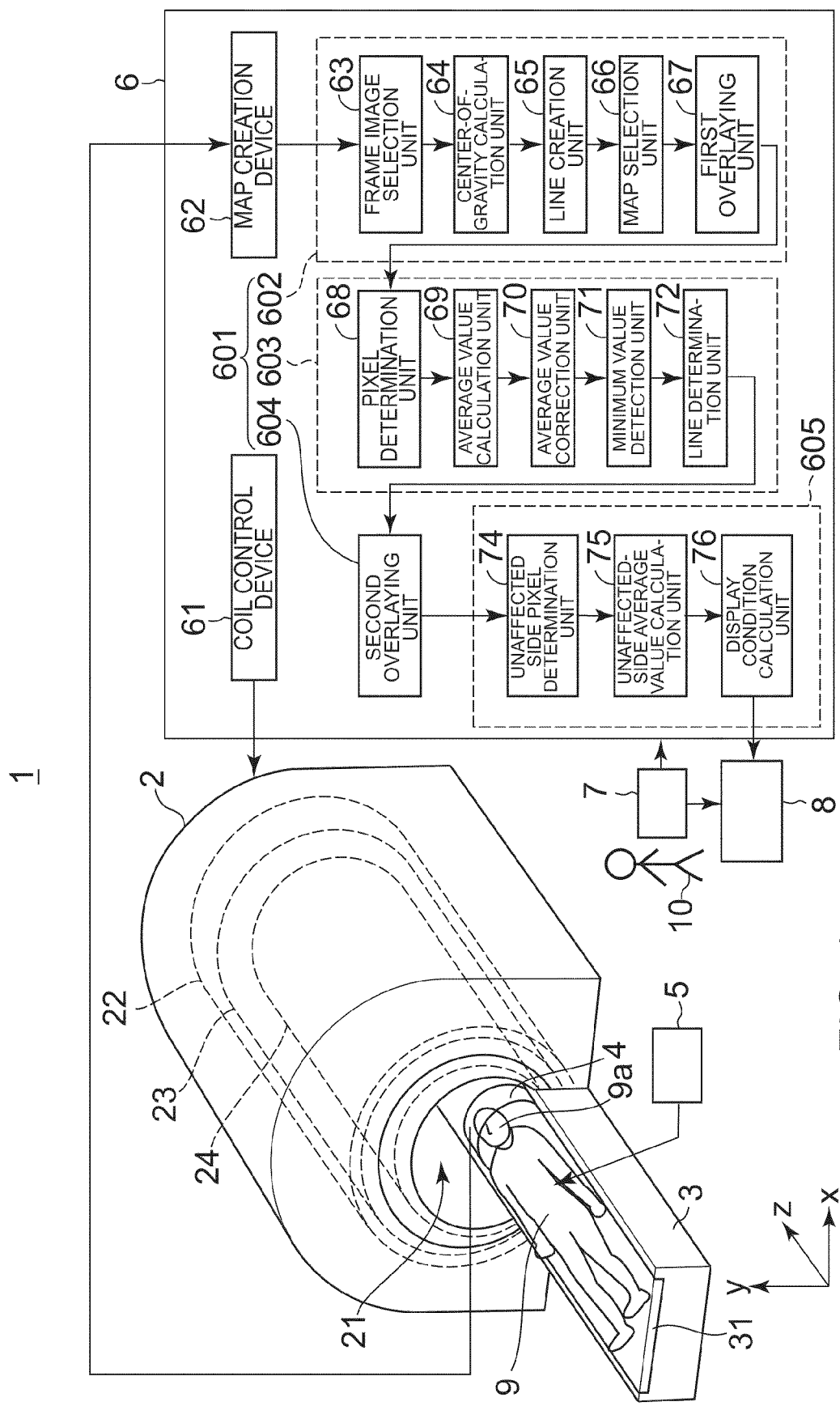
FIG. 1 is a schematic diagram of an exemplary magnetic resonance imaging system 1.

FIG. 1 is a schematic diagram of a magnetic resonance imaging system 1 according to a first embodiment of the invention.

The magnetic resonance imaging system (hereinafter called "MRI (Magnetic Resonance Imaging) system") has a coil assembly 2, a table 3, a reception coil 4, a contrast agent injection device 5, a controller 6, an input device 7 and a display device 8.

The coil assembly 2 has a bore 21 in which a subject 9 is accommodated, a superconductive coil 22, a gradient coil 23 and a transmission coil 24. The superconductive coil 22 applies a static magnetic field B0, the gradient coil 23 applies a gradient pulse and the transmission coil 24 transmits an RF pulse.

The table 3 has a cradle 31. The cradle 31 is configured so as to move in a z direction and a −z direction. With the movement of the cradle 31 in the z direction, the subject 9 is conveyed to the bore 21. With the movement of the cradle 31 in the −z direction, the subject 9 conveyed to the bore 21 is carried out of the bore 21.

The contrast agent injection device 5 injects a contrast agent into the subject 9.

The reception coil 4 is attached to the head 9a of the subject 9. An MR (Magnetic Resonance) signal received by the reception coil 4 is transmitted to the controller 6.

The controller 6 has a coil control device 61, a map creation device 62, an unaffected side detection device 601 and a display condition determination device 605.

The coil control device 61 controls the gradient coil 23 and the transmission coil 24 in response to an imaging command inputted from the input device 7 by an operator 10 in such a manner that a pulse sequence for photographing the subject 9 is executed.

The map creation device 62 calculates characteristic amounts each related to the dynamic state of the contrast agent or blood flow for every S1, . . . , Sn of slices, based on data (refer to FIG. 4A) about frame images [S1, t11] through [Sn, tnm] and creates maps indicative of the characteristic amounts. The map creation device 62 is realized by installing a program for creating the maps in the controller 6. However, it may be realized by only hardware without using the program.

The unaffected side detection device 601 detects an unaffected side of the subject 9 from within the maps created by the map creation device 62. The unaffected side creation device 601 has a line setting device 602, a line selection device 603 and a second overlaying unit 604 to detect the unaffected side.

The line setting device 602 sets a plurality of lines for detecting the unaffected side of the subject 9 to the maps created by the map creation device 62. The line setting device 602 has a frame image selection unit 63, a center-of-gravity calculation unit 64, a line creation unit 65, a map selection unit 66 and a first overlaying unit 67 to set the plural lines to the maps.

The frame image selection unit 63 selects one frame image from within the frame images [S1, t11] through [Sn, tnm].

The center-of-gravity calculation unit 64 calculates the center of gravity of the frame image selected by the frame image selection unit 63.

The line creation unit 65 creates a plurality of lines for detecting the unaffected side of the subject 9 with respect to the frame image whose center of gravity has been calculated.

The map selection unit 66 selects a map with plural lines set thereto from within the maps created by the map creation device 62.

The first overlaying unit 67 overlays the map selected by the map selection unit 66 and the plural lines created by the line creation unit 65.

The line setting device 602 has the frame image selection unit 63 through the first overlaying unit 67 configured as described above.

The unaffected side detection device 601 also has the line selection device 603 in addition to the line setting device 602.

The line selection device 603 selects lines existing in the unaffected side of the subject 9 from within a plurality of lines set to each map by the line setting device 602. The line selection device 603 has a pixel determination unit 68 through a line determination unit 72 to select the corresponding lines.

The pixel determination unit 68 determines pixels to be overlaid on their corresponding lines every line set to each map by the line setting device 602.

The average value calculation unit 69 calculates, every line, the average values of pixel values of the pixels overlaid on the lines.

The average value correction unit 70 corrects each average value of the pixel values, which has been calculated by the average value calculation unit 69.

The minimum value detection unit 71 detects the minimum value of each average value corrected by the average value correction unit 70.

The line determination unit 72 determines lines existing in the unaffected side from within the plural lines, based on the minimum value detected by the minimum value detection unit 71.

The line selection device 603 has the pixel determination unit 68 through the line determination unit 72 configured in the above-described manner.

The second overlaying unit 604 overlays the lines determined by the line determination unit 72 on another map different from the map selected by the map selection unit 66.

Incidentally, the unaffected side detection device 601 is realized by installing a program for executing the operation of each of the line setting device 602, a line selection device 603 and a second overlaying unit 604 in the controller 6. However, it may be realized by only hardware without using the program.

The display condition determination device 605 determines a display condition used when each map is displayed, based on the pixel values of the pixels existing in the unaffected side in the corresponding map. The display condition determination device 605 has an unaffected side pixel determination unit 74, an unaffected-side average value calculation unit 75 and a display condition calculation unit 76.

The unaffected side pixel determination unit 74 determines pixels overlaid on their corresponding lines existing in the unaffected side, of a plurality of pixels contained in each map.

The unaffected-side average value calculation unit 75 calculates the average values of pixel values of the pixels overlaid on the lines existing in the unaffected side.

The display condition calculation unit 76 substitutes each of the average values calculated by the unaffected-side average value calculation unit 75 into the corresponding equations (2) and (3) to calculate a window level WL and a window width WW.

Incidentally, the display condition determination device 605 is realized by installing a program for executing each of the operations of the unaffected side pixel determination unit 74, the unaffected-side average value calculation unit 75 and the display condition calculation unit 76 into the controller 6. However, it may be implemented by only hardware without using the program.

The input device 7 inputs various commands to the controller 6 according to the operation of the operator 10.

The display device 8 displays each map in accordance with the window level WL and the window width WW both calculated by the display condition calculation unit 76.

The MRI system 1 is configured as described above. The operation of the MRI system 1 will next be explained.

Figure 2:
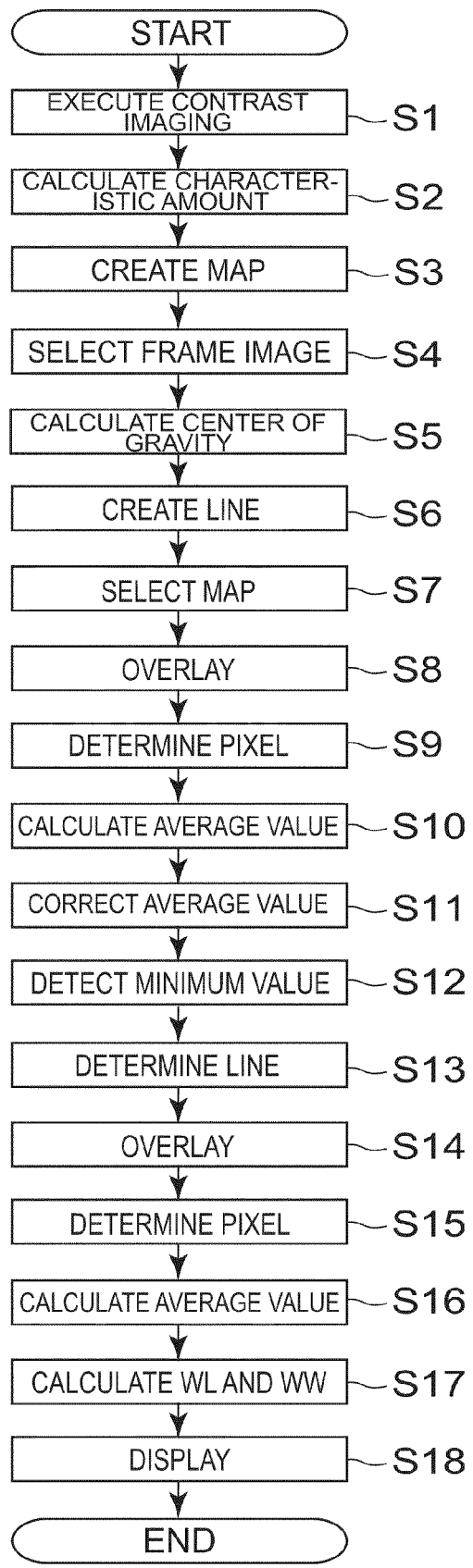
FIG. 2 is a diagram showing a processing flow of the MRI system 1.

FIG. 2 is a diagram showing a processing flow of the MRI system 1.

At Step S1, contrast imaging for the head 9a of the subject 9 is performed. The operator 10 operates the input device 7 (refer to FIG. 1) to set each slice to the subject 9.

Figure 3:
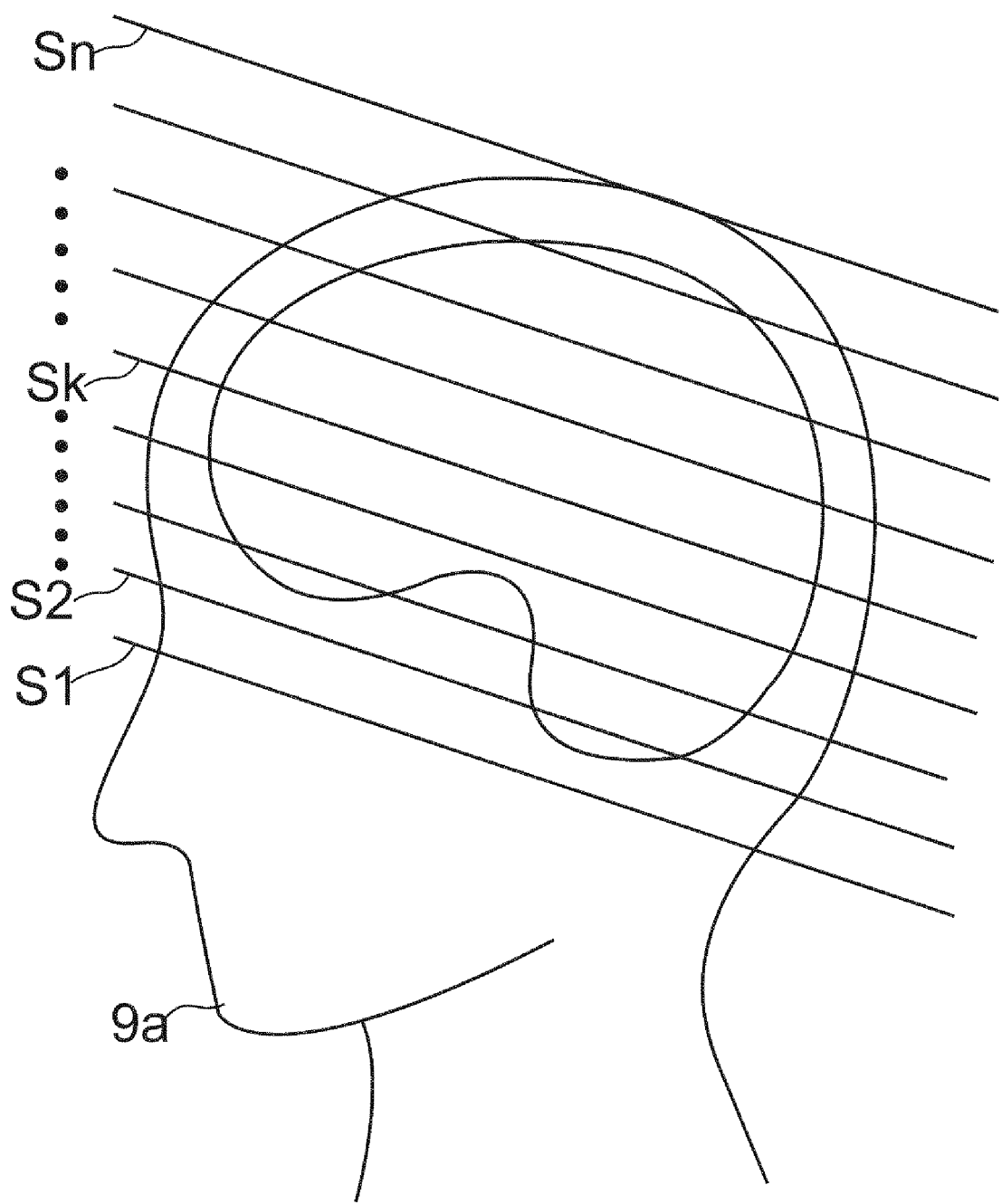
FIG. 3 is one example illustrative of slices set to a subject 9.

FIG. 3 is one example illustrative of slices set to the subject 9.

n slices S1 through Sn are set to the subject 9. The number of slices is n=12, for example. The number of slices can be set to an arbitrary number of slices as needed.

After the slices S1 through Sn have been set, the operator 10 injects a contrast agent from the contrast agent injection device 5 to the subject 9 and transmits an imaging command for photographing or imaging the subject 9 to the coil control device 61 (refer to FIG. 1) of the MRI system 1. The coil control device 61 controls the gradient coil 23 and the transmission coil 24 in response to the imaging command in such a manner that a pulse sequence for imaging the head 9a of the subject 9 is executed.

In the first embodiment, a pulse sequence for obtaining m sheets of frame images from respective slices by multi-slice scan is executed. Thus, the m sheets of frame images are obtained per slice. For example, the number of frame images m=85. Data about frame images are acquired from the slices S1 through Sn by executing the pulse sequence.

FIGS. 4A, 4B, and 4C are conceptual diagrams showing the frame images obtained from the slices S1 through Sn.

FIG. 4A is a schematic diagram showing frame images acquired from n sheets of slices S1 through Sn set to the head 9a of the subject 9 side by side on a time sequence basis in accordance with the order of their collection, FIG. 4B is a schematic diagram showing the manner in which the frame images shown in FIG. 4B are sorted for every S1, . . . , Sn of slices, and FIG. 4C is a schematic diagram showing frame images collected from a slice Sk, respectively.

Frame images [S1, t11] through [Sn, tnm] are acquired from the slices S1 through Sn (refer to FIG. 3) set to the head 9a of the subject 9 (refer to FIG. 4A). In FIG. 4A, characters on the left sides of symbols indicative of the frame images respectively represent the slices from which the frame images are acquired, whereas characters on the right sides thereof respectively represent the times at which the frame images are acquired.

FIG. 4B shows the manner in which the frame images [S1, t11] through [Sn, tnm] arranged on the time sequence basis in FIG. 4A are sorted for every S1, . . . , Sn of slices. The correspondences between the frame image of the slice Sk of the slices S1 through Sn and the frame images [S1, t11] through [Sn, tnm] in FIG. 4A are shown using arrows.

The section of the slice Sk and m sheets of frame images [Sk, tk1] through [Sk, tkm] acquired from the slice Sk are shown in FIG. 4C. The section of the slice Sk is divided into $\alpha \times \beta$ areas or zones Z1, Z2, . . . Zz. The frame images [Sk, tk1] through [Sk, tkm] respectively have $\alpha \times \beta$ pixels P1, P2, . . . Pz. The pixels P1, P2, . . . Pz of the frame images [Sk, tk1] through [Sk, tkm] are equivalent to those obtained by photographing the zones Z1, Z2, . . . Zz of the slice Sk at times tk1 through tkm (time intervals $\Delta t$).

Incidentally, although only the frame images obtained at the slice Sk are shown in FIGS. 4A, 4B, and 4C, m sheets of frame images are obtained even at other slices in a manner similar to the slice Sk.

After the execution of Step S1, the processing flow proceeds to Step S2.

At Step S2, the map creation device 62 (refer to FIG. 1) first calculates characteristic amounts each related to the dynamic state of a contrast agent or blood flow for every Z1, . . . , Zz of the zones of the slices S1 through Sn, based on the data (refer to FIG. 4(a)) about the frame images [S1, t11] through [Sn, tnm]. In the first embodiment, five characteristic amounts to be described below are calculated:

(1) Cerebral Blood Volume CBV
(2) Cerebral Blood Flow CBF
(3) Mean Transit Time MTT
(4) Bolus Arrival Time BAT and
(5) Time To Peak TTP These characteristic amounts are characteristic amounts well known in the field of a blood flow dynamic analysis. They can be calculated using the method known per se. A specific procedure for calculating the above characteristic amounts will therefore be omitted. After the characteristic amounts have been calculated, the processing flow proceeds to Step S3.

At Step S3, the map creation device 62 (refer to FIG. 1) creates maps indicative of the five characteristic amounts for every S1, . . . , Sn of slices.

Figure 5A:
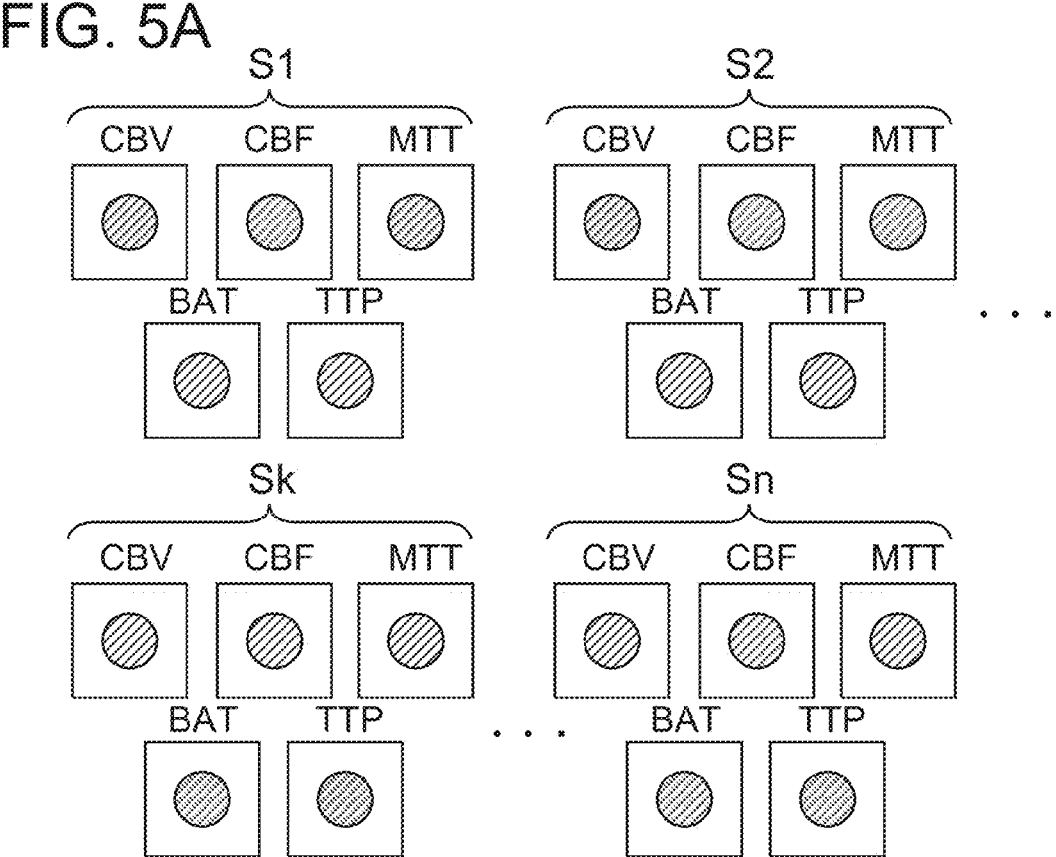
FIGS. 5A and 5B are diagrams for describing five maps created every S1, ..., Sn of slices.
Figure 5B:
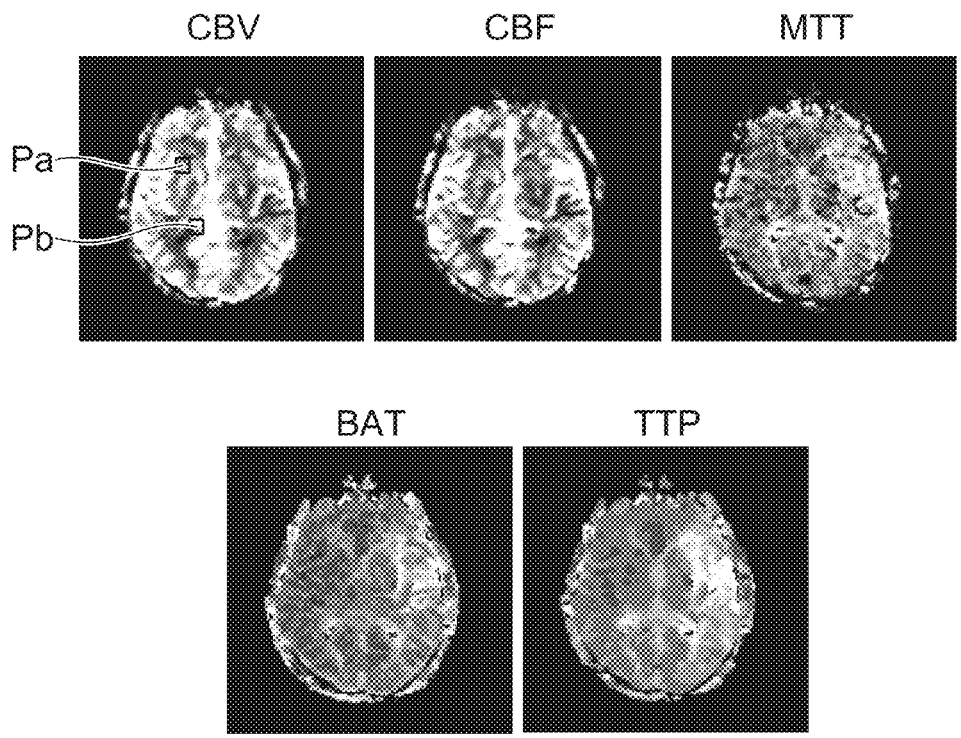

FIGS. 5A and 5B are diagrams for describing five maps created for every S1, . . . , Sn of slices.

FIG. 5A is a diagram schematically showing the five maps created for every S1, . . . , Sn of slices.

The map creation device 62 creates five maps (CBV map, CBF map, MTT map, BAT map and TTP map) for every S1, . . . , Sn of slices. The respective maps represent the following characteristic amounts:

CBV map: Cerebral Blood Volume CBV
CBF map: Cerebral Blood Flow CBF
MTT map: Mean Transit Time MTT
BAT map: Bolus Arrival Time BAT and
TTP map: Time To Peak TTP FIG. 5B is a diagram schematically showing five maps for a slice Sk.

The pixel values of respective pixels in the CBV map respectively indicate cerebral blood volumes CBV at respective zones Z in the slice Sk. For example, the pixel value of a pixel Pa in the CBV map indicates the cerebral blood volume CBV at a zone Za (refer to FIG. 4C) in the slice Sk, whereas the pixel value of a pixel Pb indicates the cerebral blood volume CBV at a zone Zb (refer to FIG. 4C) in the slice Sk. In FIG. 5B, differences in the magnitude between the pixel values of the pixels in the CBV map are represented in shades of pixels. The larger the cerebral blood flow CBV, the closer the color of each pixel to the white. The smaller the cerebral blood volume CBV, the closer the color of each pixel to the black.

Although the CBV map has been described above, other maps can be explained in a manner similar to the CBV map.

Incidentally, although the five maps about the slice Sk are shown in FIG. 5B, five maps are created even for other maps in a manner similar to the slice Sk. After the five maps are created for every S1, . . . , Sn of slices in this way, the processing flow proceeds to Step S4.

At Step S4, the frame image selection unit 63 (refer to FIG. 1) selects a sheet of frame image from the frame images [Sk, tk1] through [Sk, tkm] (refer to FIG. 4C) acquired from the slice Sk in the slices S1 through Sn.

FIG. 6 is a schematic diagram of the selected frame image.

In the first embodiment, the frame image [Sk, tkg] (refer to FIG. 4B) at the time tg is selected from within the frame images [Sk, tk1] through [Sk, tkm] acquired from the slice Sk. However, the frame image at another time within the frame images [Sk, tk1] through [Sk, tkm] may be selected. Alternatively, the frame images acquired from other slices other than the slice Sk may be selected. After the selection of the frame image [Sk, tkg], the processing flow proceeds to Step S5.

At Step S5, the center-of-gravity calculation unit 64 (refer to FIG. 1) calculates the center of gravity of the frame image [Sk, tkg].

FIG. 7 is a diagram showing the position of the calculated center of gravity G.

As a method of calculating the center of gravity G, a known center-of-gravity calculating method such as a method for calculating the frame image [Sk, tkg] by its binarization can be used. After the calculation of the center of gravity G, the processing flow proceeds to Step S6.

At Step S6, the line creation unit 65 (refer to FIG. 1) creates a plurality of lines that extend from the center of gravity G of the frame image [Sk, tkg].

FIG. 8 is a diagram showing the frame image [Sk, tkg] in which the plural lines are created.

In the first embodiment, sixteen lines L1 through L16 are created so as to extend radially with respect to the center of gravity G. These lines L1 through L16 are lines used to detect an unaffected side (corresponding to a portion free of a disease such as a lesion or the like) from within the section of a head shown in each map at Step S13 to be described later. The angle θ formed between the adjacent lines is θ=22.5°. After the formation of the lines L1 through L16, the processing flow proceeds to Step S7.

At Step S7, the map selection unit 66 (refer to FIG. 1) selects a map for detecting the unaffected side of the head from the maps created at Step S3. Any map created at Step S3 can be taken as a candidate for the map for detecting the unaffected side of the head. Since, however, the sixteen lines L1 through L16 used to detect the unaffected side of the head are created with respect to the frame image [Sk, tkg] of the slice Sk (refer to FIG. 8), the corresponding map for detecting the unaffected side of the head is preferably selected from within the five maps (refer to FIG. 5B) of the slice Sk. Thus, the map selection unit 66 selects one map from within the five maps of the slide Sk. In the first embodiment, the map selection unit 66 selects an MTT map. After the selection of the corresponding map, the processing flow proceeds to Step S8.

At Step S8, the first overlaying unit 67 (refer to FIG. 1) overlays the lines L1 through L16 and the MTT map of the slice Sk on one another.

Figure 9:
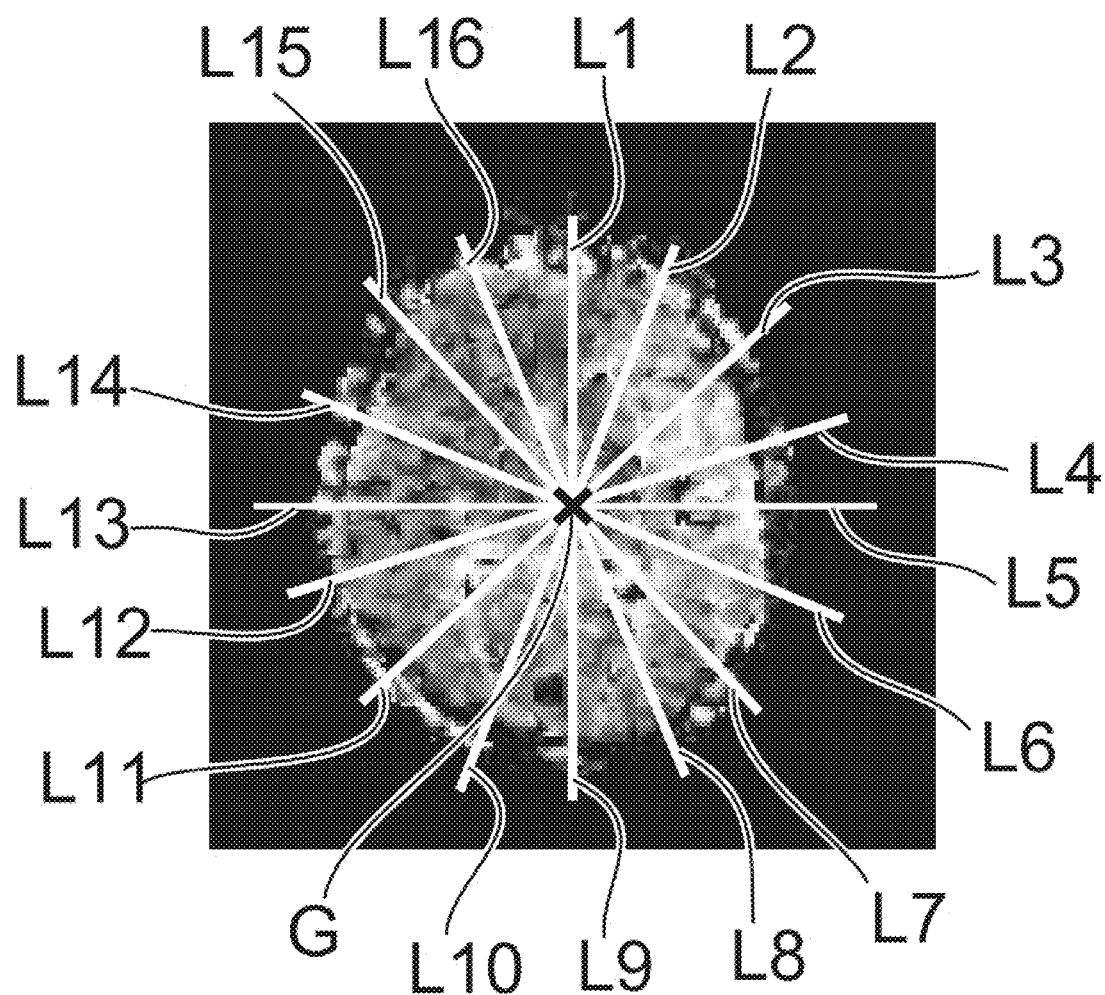
FIG. 9 is a diagram showing the manner in which lines L1 through L16 and an MTT map of a slice Sk are overlaid on one another.

FIG. 9 is a diagram showing the manner in which the lines L1 through L16 and the MTT map of the slice Sk are overlaid on one another.

After the lines L1 through L16 and the MTT map of the slice Sk have been overlaid, the processing flow proceeds to Step S9.

At Step S9, the pixel determination unit 68 (refer to FIG. 1) determines pixels overlaid on the lines from within a plurality of pixels contained in the MTT map every L1, . . . , L16 of lines. A description will hereinafter be made of how to determine the pixels overlaid on the lines.

Figure 10:
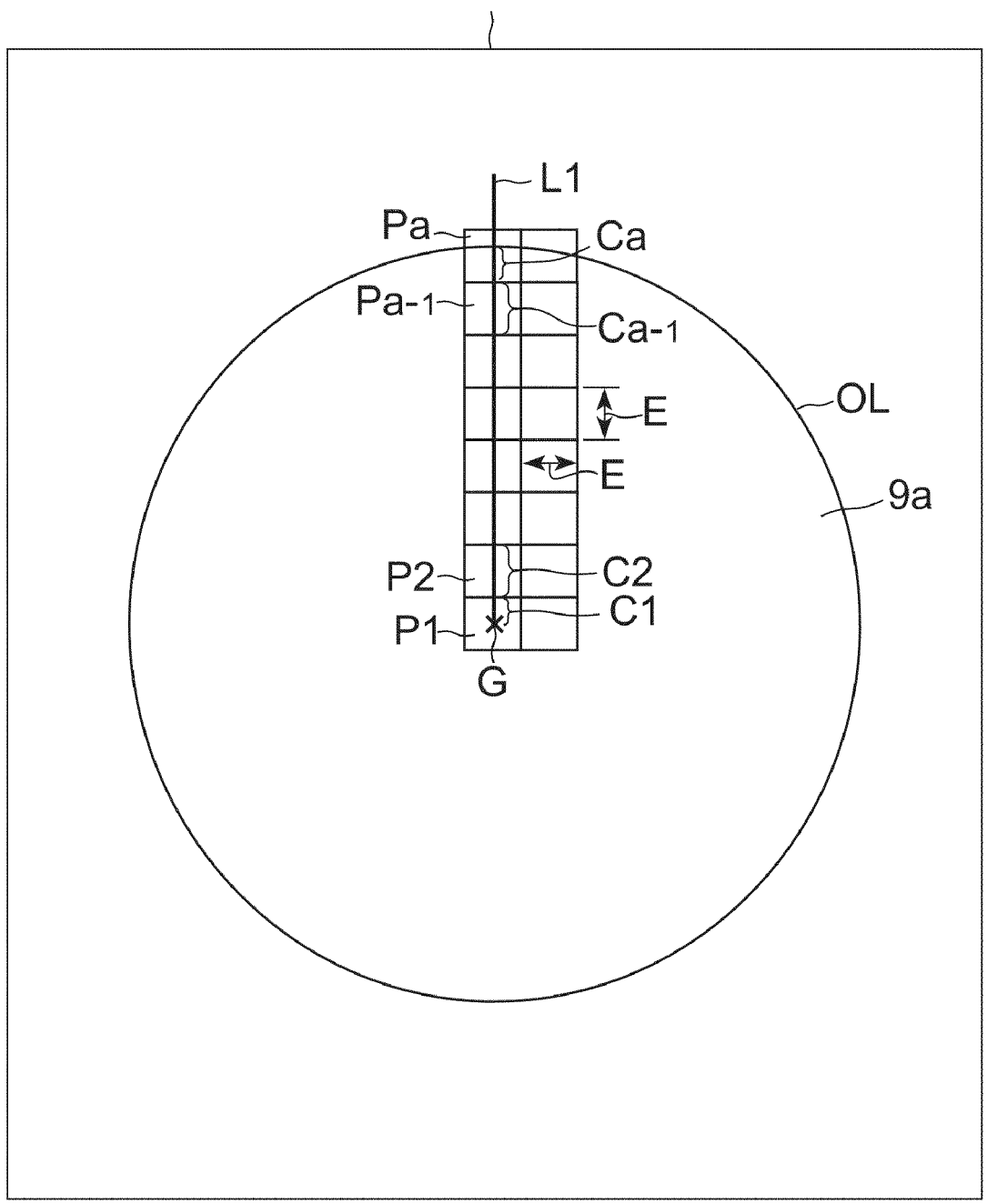
FIG. 10 is a diagram schematically illustrating the line L1 and the MTT map.

The pixel determination unit 68 first determines pixels overlaid on the line L1 from a range lying inside the head shown in the MTT map (refer to FIG. 10).

FIG. 10 is a diagram schematically showing the line L1 and the MTT map.

Only the outline OL of the head 9a of the subject 9 is shown in the MTT map of FIG. 10. All pixels in the MTT map are not shown in FIG. 10 and only some pixels existing in the neighborhood of the line L1 are shown in square form. Incidentally, although the size of each pixel is actually made smaller, the pixels are shown widely in FIG. 10 for convenience of explanation.

The pixel determination unit 68 first extracts pixels across which the line L1 cuts. Since the line L1 crosses pixels P1, P2, . . . Pa in the first embodiment, the pixels P1, P2, . . . Pa are extracted. After the extraction of the pixels P1 through Pa, the lengths of line segments C1 through Ca relative to the pixels P1 through Pa, of the line L1 are calculated. Incidentally, the pixel Pa exists astride the inner and outer sides of the head 9a. In this case, only a portion that cuts across the head 9a within the pixel Pa is defined as the length of the line segment Ca. Thus, after the lengths of the line segments C1 through Ca have been calculated, it is determined whether each of the calculated lengths of line segments C1 through Ca is a length greater than or equal to a predetermined threshold value Lth. The threshold value Lth is expressed in the following equation (1), for example:

$$Lth = (1/2)E \qquad (1)$$

where E indicates the length of one side of each pixel.

In the first embodiment, only each pixel in the pixels P1 through Pa, at which the length of each line segment becomes greater than or equal to the threshold value Lth, is decided as the pixel overlaid on the line L1. In the first embodiment, the lengths of the line segments C1 through Ca are all assumed to be larger than the threshold value Lth. Thus, the pixel determination unit 68 determines all pixels P1 through Pa across which the line L1 cuts, as the pixels overlaid on the line L1.

Next, the pixel determination unit 68 determines pixels overlaid on the line L2 from the range lying inside the head 9a shown in the MTT map.

Figure 11:
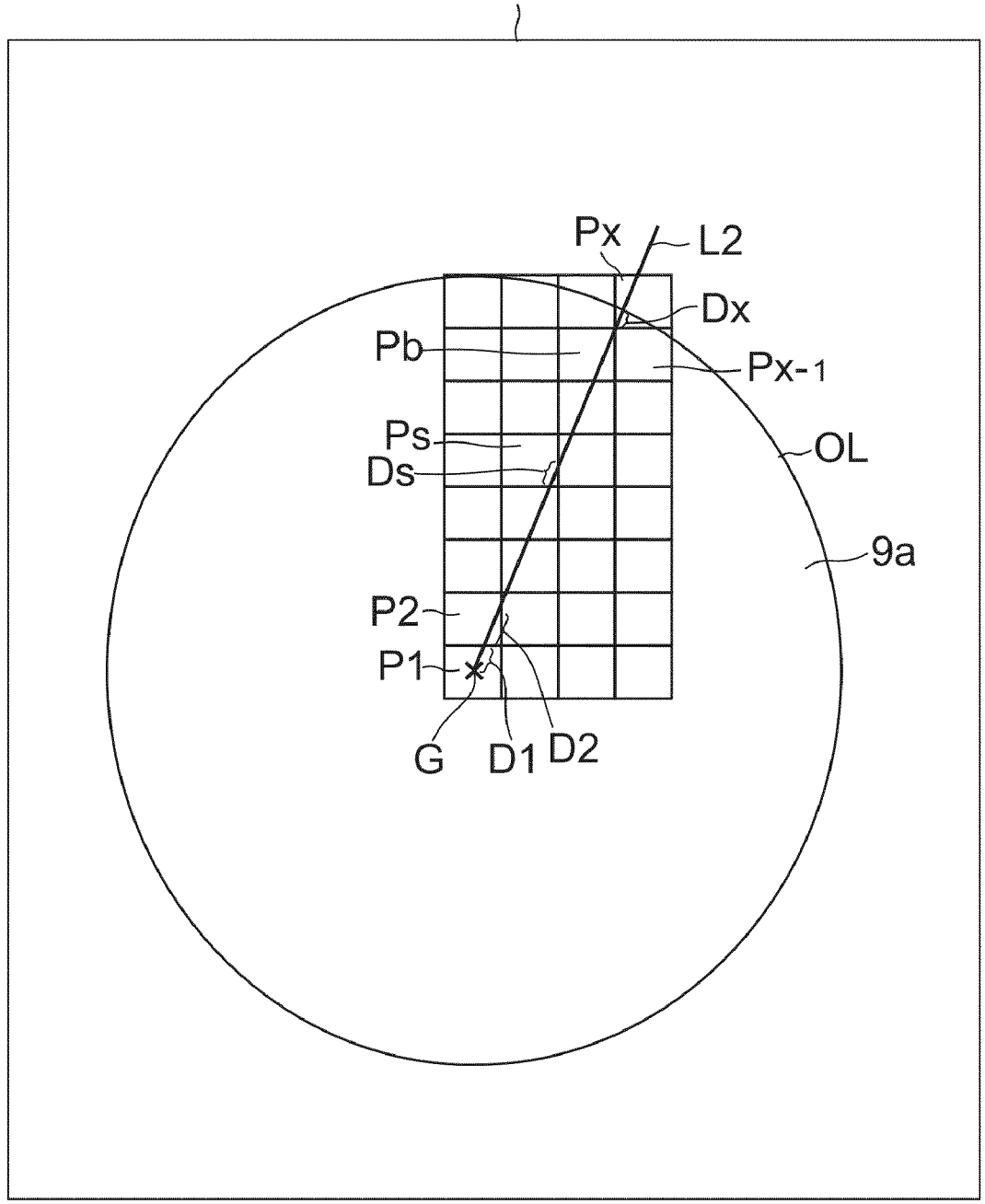
FIG. 11 is a diagram schematically depicting the line L2 and the MTT map.

FIG. 11 is a diagram schematically showing the line L2 and the MTT map.

All pixels contained in the MTT map are not shown in FIG. 11 and only some pixels existing in the neighborhood of the line L2 are shown therein.

The pixel determination unit 68 extracts pixels across which the line L2 cuts. In the first embodiment, the line L2 cuts across pixels P1 through Px. Thus, the pixels P1 through Px are extracted. After the extraction of the pixels P1 through Px, the lengths of line segments D1 through Dx relative to the pixels P1 through Px, of the line L2 are calculated. Incidentally, since the pixel Px exists astride the inner and outer sides of the head 9a, only a portion that cuts across the head 9a within the pixel Px is defined as the length of the line segment Dx. Thus, after the lengths of the line segments D1 through Dx have been calculated, it is determined whether each of the calculated lengths of line segments D1 through Dx is a length greater than or equal to the predetermined threshold value Lth (refer to the equation (1)). Only each pixel at which the length of each line segment becomes greater than or equal to the threshold value Lth, is determined as the pixel overlaid on the line L2. Since, for example, the length of the line segment D1 at the pixel P1 is larger than the threshold value Lth, the pixel P1 is decided as the pixel overlaid on the line L2. Since, however, the length of the line segment Ds at the pixel Ps is smaller than the threshold value Lth, the pixel Ps is determined not to be the pixel overlaid on the line L2. It is determined whether other pixels correspond to the pixels overlaid on the line L2.

The pixels overlaid on the respective lines are determined even with respect to other lines L3 through L16 in like manner subsequently.

FIG. 12 is a table showing, every line, pixels determined to be overlaid on the lines L1 through L16.

Three items "line", "pixel" and "number of pixels" are shown in FIG. 12. The item "line" represents the lines L1 through L16. The item "pixel" represents pixels determined to be overlaid on the respective lines. The item "number of pixels" indicates the number of pixels determined to be overlaid on the respective lines.

As shown in FIG. 12, the pixels overlaid on the lines L1 through L16 are determined by the pixel determination unit 68. After the pixels overlaid on the lines L1 through L16 have been decided, the processing flow proceeds to Step S10.

At Step S10, the average value calculation unit 69 (refer to FIG. 1) calculates the average values of pixel values of pixels overlaid on their corresponding lines for every L1, . . . , L16 of lines.

FIG. 13 is a table showing the average values of pixel values calculated every line.

Four items "line", "pixel", "number of pixels" and "average value of pixel values" are shown in FIG. 13. Since the items "line", "pixel" and "number of pixels" are identical to those shown in FIG. 12, their explanations are omitted.

The item "average value of pixel values" indicates the average value of pixels values calculated every line. As shown in FIG. 13, for example, pixels P1 through Pa corresponding to the number of pixels N1 are determined to be overlaid on the line L1 in the case of the line L1. Thus, the first average value calculation unit 69 calculates an average value V1 of pixel values of the N1 pixels P1 through Pa. The first average value calculation unit 69 calculates average values V2 through V16 of pixel values even with respect to other lines L2 through L16 in like manner subsequently.

Figure 14:
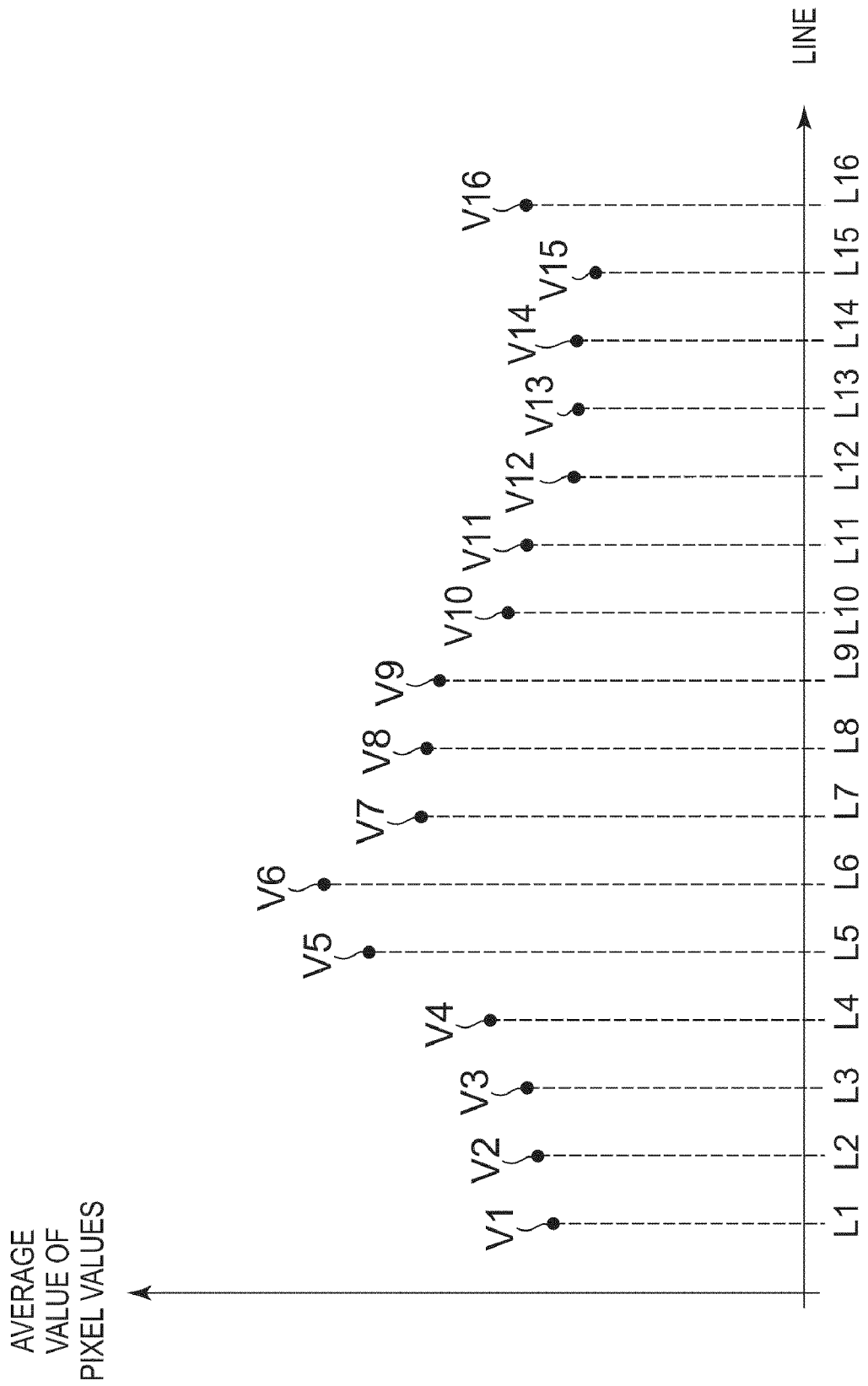
FIG. 14 is a diagram illustrating graphs of the average values V1 through V16 of the pixel values calculated every line.

FIG. 14 is a diagram showing graphs of the average values V1 through V16 of the pixel values calculated every line.

The horizontal axis of each graph indicates the line, and the vertical axis thereof indicates the average value of pixel values. Referring to FIG. 14, it is understood that the values of the average values V1 through V16 are different from one another every line. The values of the average values V1 through V16 are, in the step 13 which will be described later, values used to determine the lines each existing on the unaffected side of the head of the subject from within the lines L1 through L16 (refer to FIG. 9). Using the values of the average values V1 through V16 makes it possible to determine each line existing on the unaffected side of the head of the subject from within the lines L1 through L16. This reason will be explained below while referring to FIG. 15.

Figure 15:
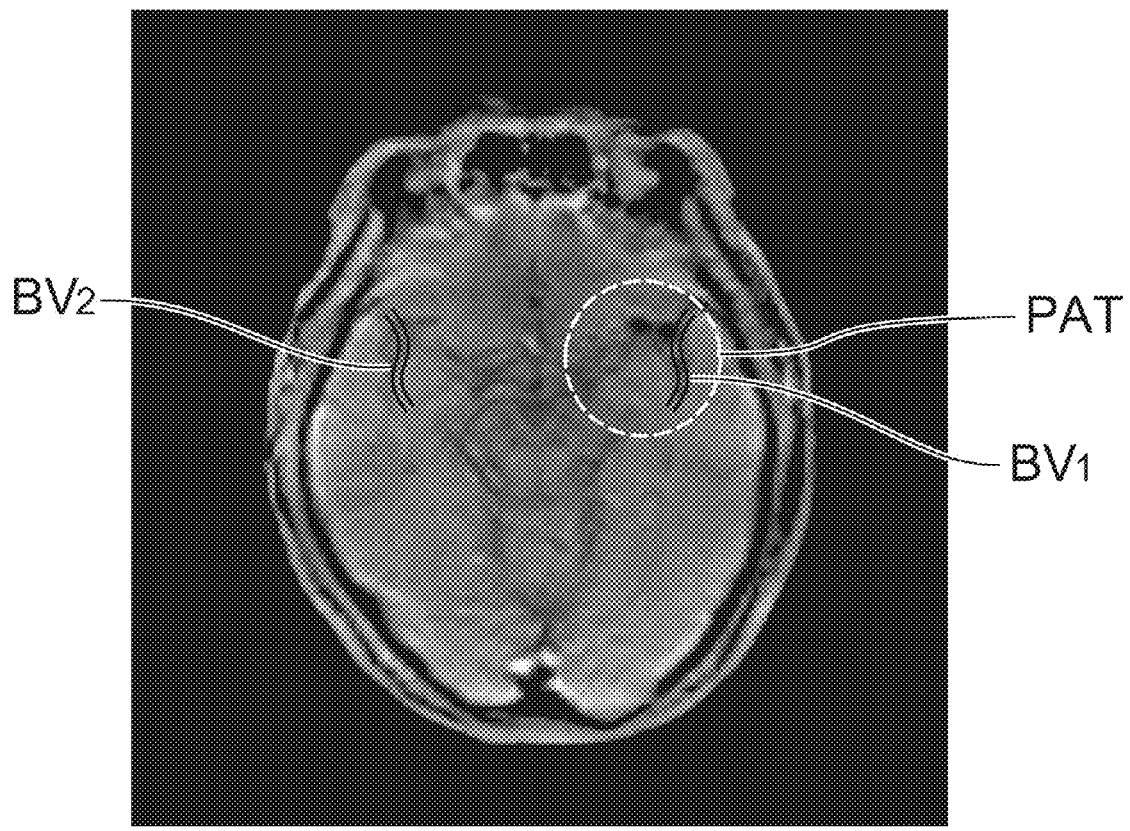
FIG. 15 is a diagram schematically showing a section of the brain in the head.

FIG. 15 is a diagram schematically showing a section of the brain in the head.

An affected side PAT is shown in FIG. 15 by a broken line. When, for example, arterial stiffness or the like occurs in the affected portion PAT, there is a case in which a blood vessel BV1 in the affected portion PAT is narrowed and hence the diameter of the blood vessel BV1 becomes narrow. When the diameter of the blood vessel BV1 becomes narrow, there is a tendency that a blood flow becomes slow. Thus, the time required for a contrast agent to pass through the affected portion PAT becomes long at the affected portion PAT. As a result, there is a tendency that the value of a mean transit time MTT becomes large.

On the other hand, since the arterial stiffness or the like that becomes a cause of narrowing of the diameter of a blood vessel BV2 does not occur in an unaffected side free of the occurrence of a disease, there is a tendency that the blood flow becomes faster than that at the affected portion PAT. Thus, the time necessary for the contrast agent to pass through the unaffected side becomes short at the unaffected side. As a result, there is a tendency that the value of a mean transit time MTT becomes small. In the first embodiment, attention has been paid to the fact that the difference in the value of the mean transit time MTT appears between the affected side and the unaffected side. Increasing each pixel value of the MTT map means that the value of the mean transit time MTT is large. On the other hand, decreasing each pixel value of the MTT map means that the value of the mean transit time MTT is small. Therefore, each line at which the average value of pixels values is small (i.e., the value of the mean transit time MTT is small) may be found out to detect the unaffected side. The minimum value of the average values V1 through V16 of pixel values becomes the average value V15 as shown in FIG. 14. Thus, the line L15 can be determined to be a line existing on the unaffected side. However, each of the average values V1 through V16 of the pixel values is also considered to contain some degree of error. Thus, in the first embodiment, the average values V1 through V16 of the pixel values are corrected before each line existing on the unaffected side is determined. In order to correct the average values V1 through V16 of the pixel values, the processing flow proceeds from Step S10 to Step S11.

At Step S11, the average value correction unit 70 (refer to FIG. 1) corrects the average values V1 through V16 of the pixel values.

Figure 16:
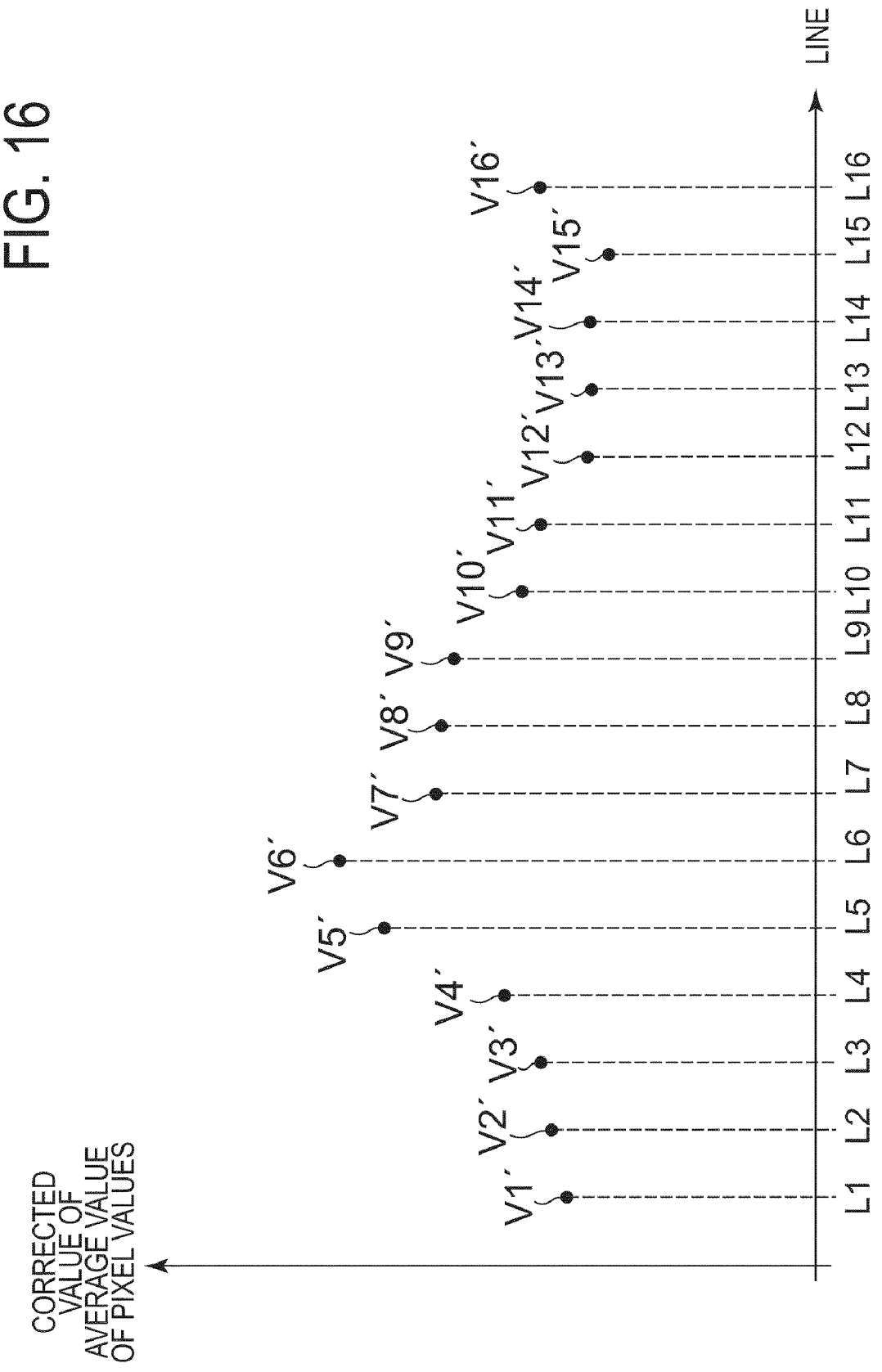
FIG. 16 is a diagram showing one example illustrative of post-correction average values V1' through V16'.

FIG. 16 is a diagram showing one example illustrative of post-correction average values V1' through V16'.

In the first embodiment, the average values V1 through V16 of the pixel values are corrected by a 5-point moving average method to obtain post-correction average values V1' through V16'. For example, the moving average is calculated with respect to the average value V1 of the pixels values using the average value V1 and using the average values lying before and after the average value V1 two by two (average values V15 and V16 and average values V2 and V3). Similarly, the moving average is calculated with respect to the average value V15 of the pixel values using the average value V15 and using the average values before and after the average value V15 two by two (average values V13 and V14 and average values V16 and V1). Incidentally, they may be corrected by another method other than the moving average method. After all the average values V1 through V16 have been corrected in this way, the processing flow proceeds to Step S12.

At Step S12, the minimum value detection unit 71 (refer to FIG. 1) detects the minimum value out of the post-correction average values V1' through V16'. Since the minimum value is V15' in the first embodiment, the minimum value detection unit 71 detects the average value V15'. After the detection of the average value V15', the processing flow proceeds to Step S13.

At Step S13, the line determination unit 72 (refer to FIG. 1) determines each line existing in the unaffected side from within the lines L1 through L16, based on the post-correction average value V15' detected at Step S12. Since the minimum value V15' of the post-correction average values is obtained by correcting the average value V15 at the line L15, the line L15 is determined to be the line existing on the unaffected side. However, the minimum value V15' is of a value calculated using not only the average value V15 of the pixel values at the line L15 but also the average values V1, V13, V14 and V16 of the pixel values at the lines L1, L13, L14 and L16. Hence, the lines L1, L13, L14 and L16 are also considered to be lines existing on the unaffected side as well as the line L15. Thus, in the first embodiment, the line determination unit 72 determines not only the line L15 but also the lines L1, L13, L14 and L16 as the lines existing on the unaffected side.

Figure 17:
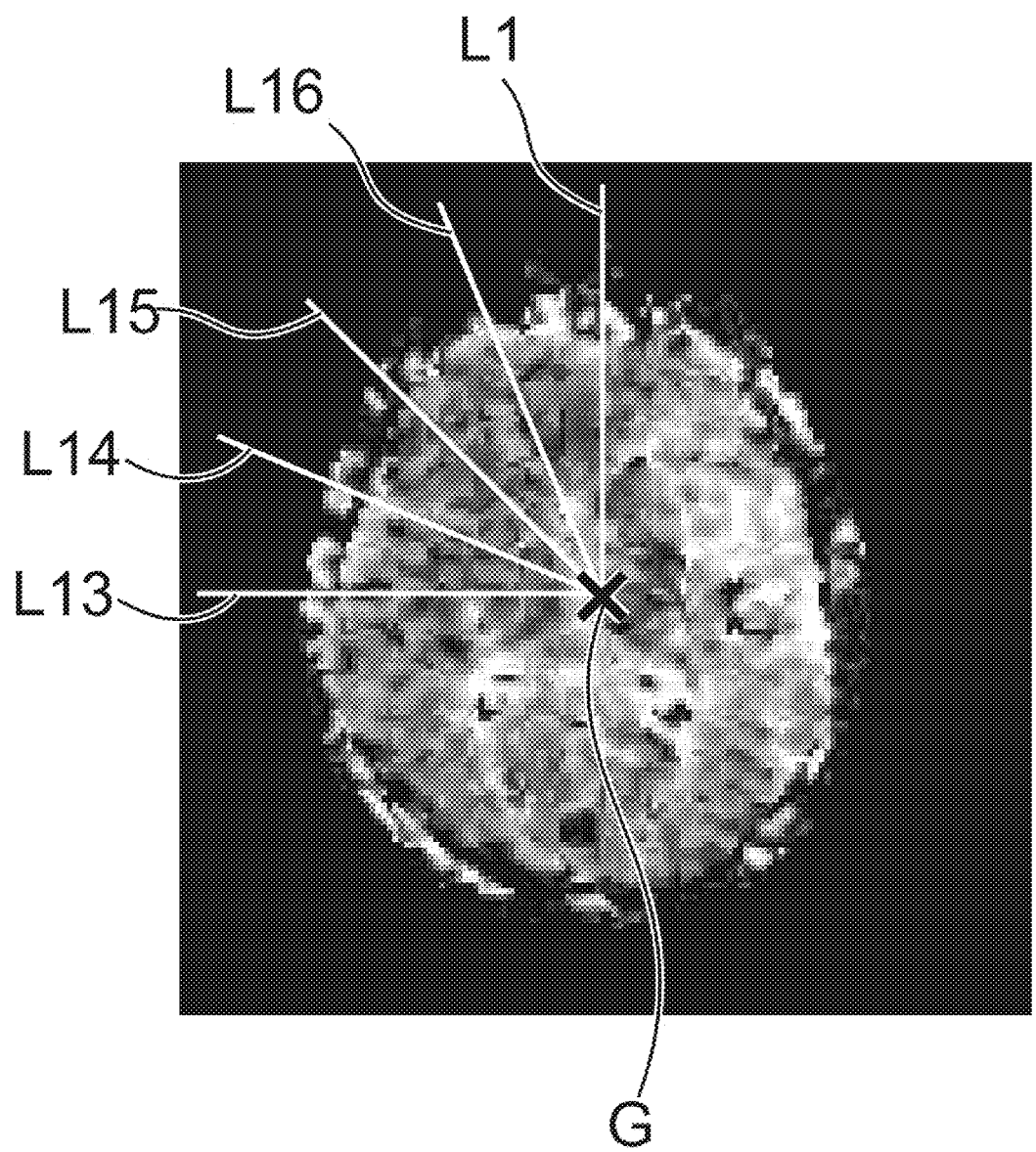
FIG. 17 is a diagram illustrating an MTT map and lines L1 and L13 through L16 existing on the unaffected side.

FIG. 17 is a diagram showing an MTT map (refer to FIG. 9) and lines L1 and L13 through L16 that exist on the unaffected side.

The lines L1 and L13 through L16 are located on the upper left of the MTT map. It is thus understood that at least the upper left side of the head corresponds to the unaffected side. After the lines L1 and L13 through L16 existing on the unaffected side have been determined, the processing flow proceeds to Step S14.

At Step S14, the second overlaying unit 604 (refer to FIG. 1) overlaps the lines L1 and L13 through L16 even on another map other than the MTT map of the slice Sk and further overlaps them even on five maps of other slices other than the slice Sk.

Figure 18A:
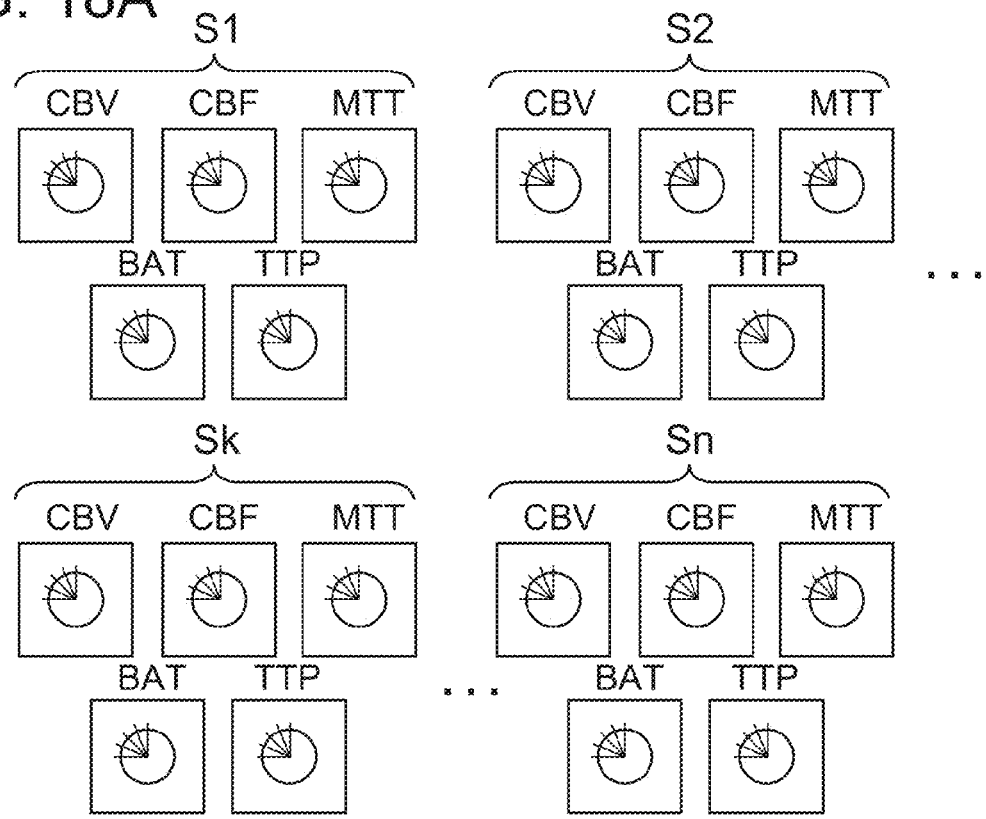
FIGS. 18A and 18B are diagrams showing the manner in which the lines L1 and L13 through L16 are overlaid on their corresponding maps of the slices S1 through Sk.
Figure 18B:
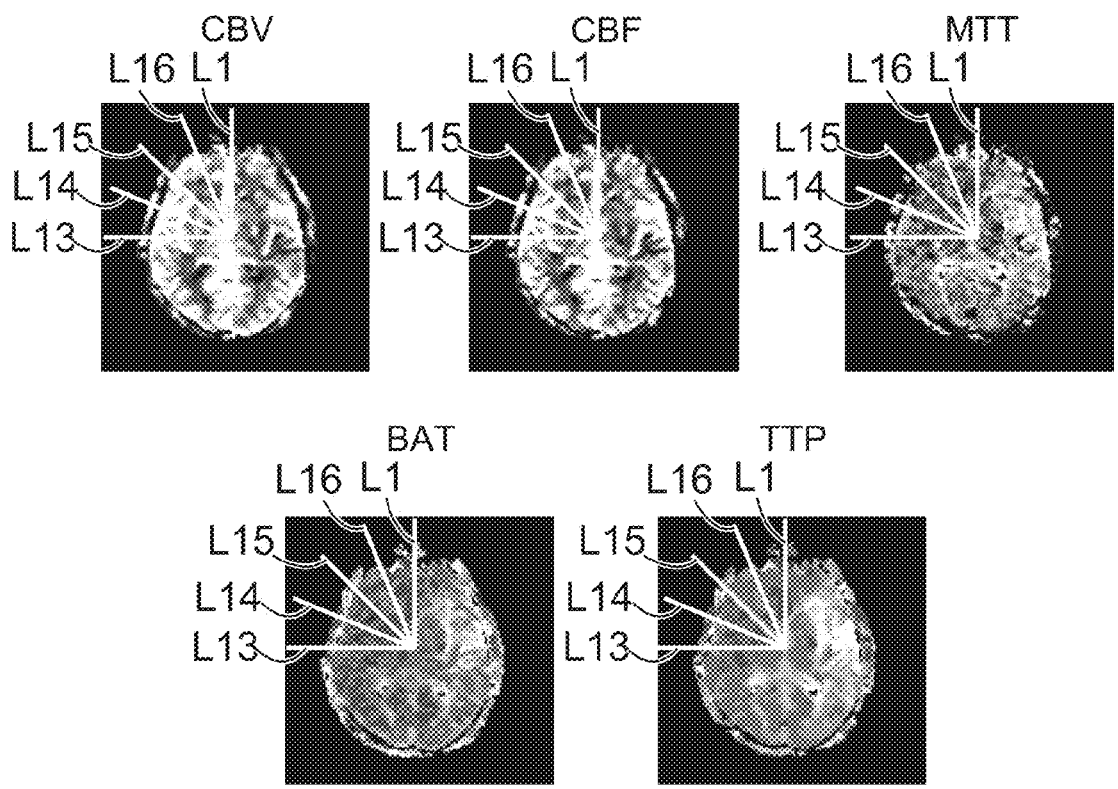

FIGS. 18A and 18B are diagrams showing the manner in which the lines L1 and L13 through L16 are overlaid on their corresponding maps of slices S1 through Sk.

Five maps on which the lines L1 and L13 through L16 are overlaid every S1, . . . , Sn of slices are schematically shown in FIG. 18A. FIG. 18B shows the five maps of the slice Sk lying in the slices S1 through Sk.

With the overlaying of the lines L1 and L13 through L16 thereon, unaffected sides can be detected with respect to all slices every map. Referring to FIG. 18B, it is understood that the lines L1 and L13 through L16 have been overlaid on the range lying forward on the left side of the head at any map of the slice Sk. It is understood that while FIG. 18B shows the manner in which the lines L1 and L13 through L16 are overlaid on the five maps of the slice Sk, the lines L1 and L13 through L16 have been overlaid on the ranges each lying forward on the left side of the head even at the five maps of other slices.

After the lines L1 and L13 through L16 have been overlaid on all the maps as shown in FIG. 18, the processing flow proceeds to Step S15.

At Step S15, the unaffected side pixel determination unit 74 (refer to FIG. 1) determines pixels overlaid on the lines L1 and L13 through L16 existing in the unaffected sides with respect to all the maps of slices S1 through Sk. Since the present pixel determining method is identical to the method described while referring to FIGS. 10 and 11 (Step S9), its description is omitted. After the corresponding pixels have been determined, the processing flow proceeds to Step S16.

At Step S16, the unaffected-side average value calculation unit 75 (refer to FIG. 1) calculates the average values (hereinafter called "unaffected side average values") U of pixel values of pixels existing in unaffected sides every map. The unaffected side average values U are calculated as described below.

Since the lines L1 and L13 through L16 correspond to the lines existing in the unaffected sides as described with reference to FIG. 16, the pixels overlaid on the lines L1 and L13 through L16 result in the pixels that exist in the unaffected sides. Thus, the average values of the pixels overlaid on the lines L1 and L13 through L16 can be considered to be the average values U of the pixel values of the pixels existing in the unaffected sides respectively. Thus, in the first embodiment, the unaffected-side average value calculation unit 75 calculates the average values of the pixels overlaid on the lines L1 and L13 through L16 as their corresponding unaffected side average values U. The unaffected side average value U is calculated as described below with respect to the MTT map of the slice Sk.

Figure 19:
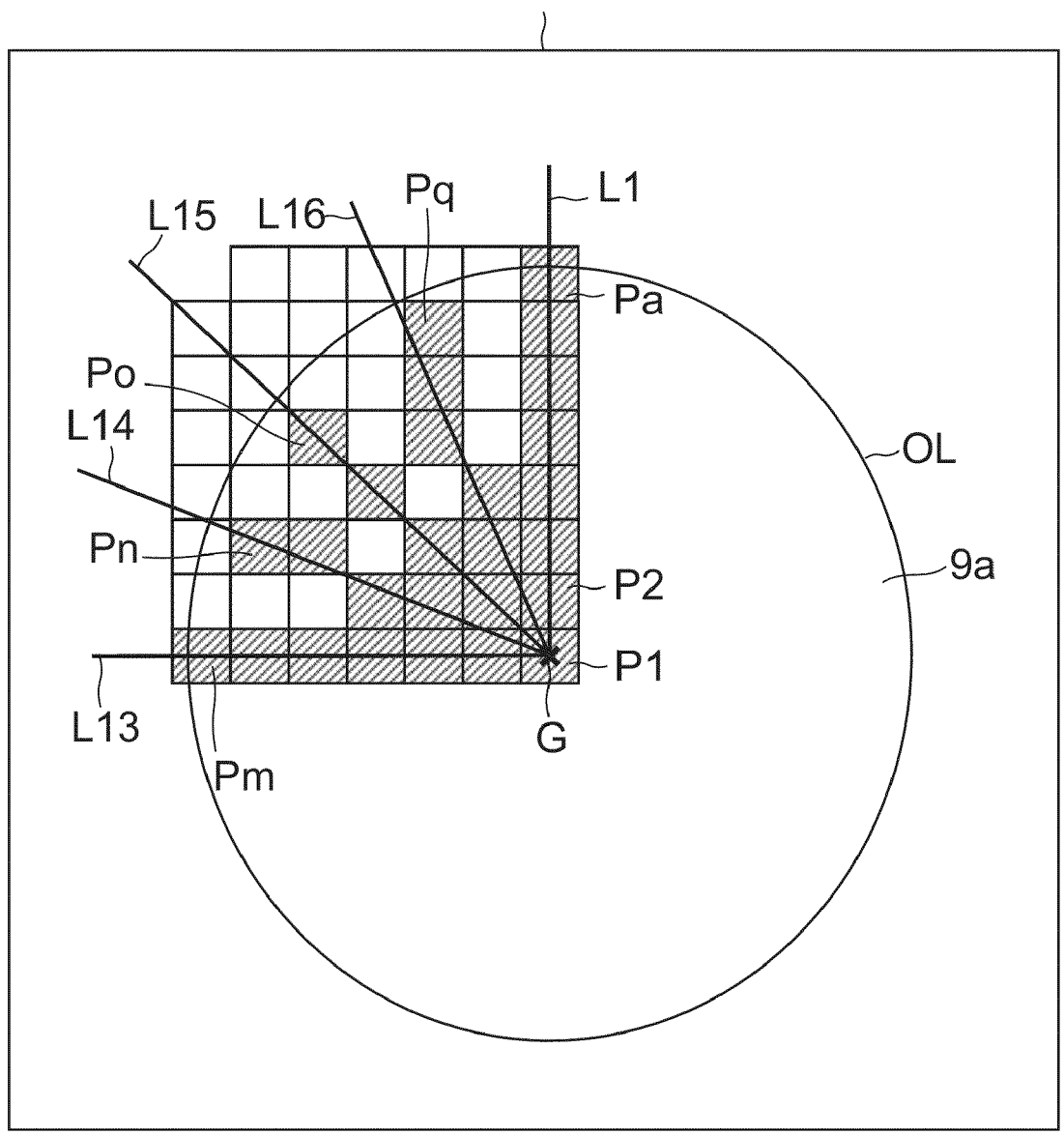
FIG. 19 is an explanatory diagram for calculating an unaffected side average value U in the MTT map of the slice Sk.

FIG. 19 is an explanatory diagram for calculating the unaffected side average value U in the MTT map of the slice Sk.

The pixels determined to be overlaid on the lines L1 and L13 through L16 are shown in diagonal lines in FIG. 19. The unaffected-side average value calculation unit 75 calculates the average values U of pixels values of all pixels shown in the diagonal lines. Thus, the unaffected-side average value calculation unit 75 calculates the average values of the pixel values of all pixels overlaid on the lines L1 and L13 through L16 without calculating the average value of the pixel values of the pixels (pixels P1 through Po overlaid on the line L15, for example) overlaid on one line. Since the lines L1 and L13 through L16 are considered to be the lines existing in each unaffected side, the unaffected side average value U can be found out by calculating the average value U of the pixel values of all pixels shown in the diagonal lines.

Although the unaffected side average value U of the MTT map for the slice Sk has been described above, the unaffected side average values U of other maps for the slice Sk and the unaffected side average values U of maps for other slices are also similar thereto. The unaffected side average values U are calculated with respect to the maps for all the slices S1 through Sn.

FIG. 20 is a table showing the unaffected side average values U calculated with respect to the maps for all slices S1 through Sn.

It is understood from FIG. 20 that the unaffected side average values U have been calculated with respect to five maps for each slice. After the calculation of the unaffected side average values U, the processing flow proceeds to Step S17.

At Step S17, the display condition calculation unit 76 calculates a window level WL and a window width WW, based on each of the unaffected side average values U calculated with respect to the five maps for the respective slices S1 through Sn. The WL and WW are calculated using the following equations:

$$WL = U \times k1 \quad (2)$$

$$WW = U \times k2 \quad (3)$$

where k1 and k2: constants.

Since the unaffected side average values U in the equations (2) and (3) are shown in FIG. 20, the unaffected side average values U calculated every map for the slices S1 through Sn are substituted into the equations (2) and (3), thereby making it possible to calculate WL and WW of the maps every slice. After the calculation of WL and WW, the processing flow proceeds to Step S18.

At Step S18, the operator 10 operates the input device 7 to input a command for displaying images for each slice to the controller 6. When the command is inputted thereto, the display control device displays the images for each slice in accordance with the command inputted by the operator. Next, display images of five maps for a slice Sk are shown as one example illustrative of display images.

Figure 21:
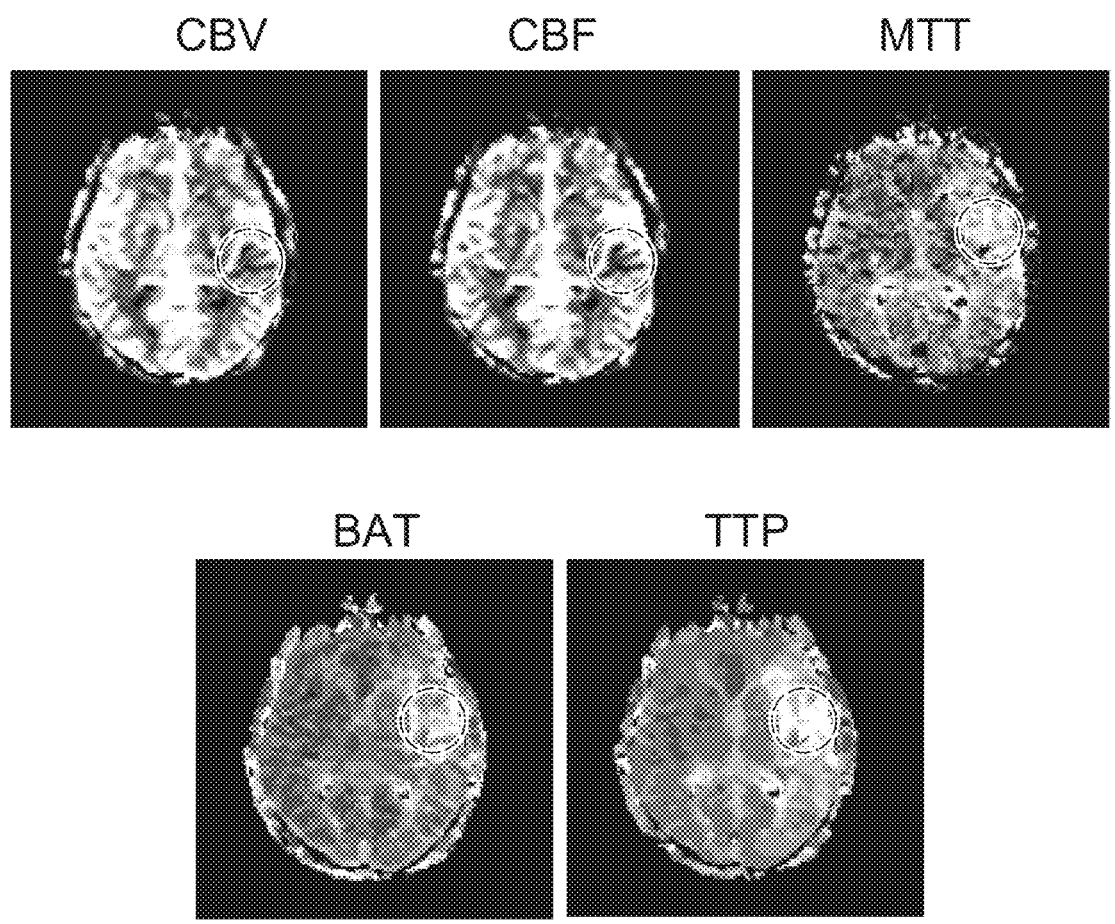
FIG. 21 is a diagram illustrating one example illustrative of displayed images of the five maps for the slice Sk.

FIG. 21 is a diagram showing one example illustrative of the display images of the five maps for the slice Sk.

It is understood from FIG. 20 that when a gradation distribution on the right brain side and a gradation distribution on the left brain side are compared, there is a high probability that a portion or side surrounded by a broke line will show a lesion at each map.

In the first embodiment, lines existing in an unaffected side are detected from a plurality of lines overlaid on maps each indicative of a characteristic amount. Window levels WL and window widths WW of the respective maps are determined based on average values of pixel values of pixels overlaid on the detected lines. Thus, when an affected side exists in a subject's imaging range, the unaffected side and the affected side are displayed in different shades of gray. Therefore, images in which unaffected and affected sides are displayed in different shades of gray are automatically displayed with no need to adjust WL and WW by the operator. Therefore, the operator can easily specify an affected side in a short period of time.

Incidentally, the values of WL and WW respectively depend on the constants k1 and k2 (refer to the equations (2) and (3)). The values of k1=1 and k2=2 can normally be adopted. However, k1 and k2 may adopt values different every map, for example.

In the first embodiment, the sixteen lines L1 through L16 are created at Step S6. If, however, the unaffected side can be detected, then the number of lines to be created may not be limited to 16, but may be set to 32, for example.

In the first embodiment, the center of gravity is calculated (Step S5) and each line is created based on the calculated center of gravity. The lines may however be created without calculating the center of gravity.

In the first embodiment, the threshold value Lth for determining whether the pixels are overlaid on each line is defined by the equation (1). However, the threshold value Lth may be defined using another equation different from the equation (1). In the first embodiment, only the pixels at each of which the length of each line segment of the line becomes larger than the threshold value Lth (refer to the equation (1)), are determined as the pixels overlaid on each line. If, however, each line cuts across pixels, then they may be determined as pixels overlaid on the line regardless of the length of each line segment of the line. Since various methods are known as the method for determining the pixels overlaid on each line, the pixels may be decided by another method different from the above method.

In the first embodiment, the average value of the pixels is calculated (refer to Step S10) and each line is determined based on the calculated average value of pixels (refer to Step S13). If, however, each line is determined based on the pixel values of the pixels, then added values of pixels are calculated in place of the calculation of the average value of the pixels, for example, and each line may be determined based on the added values. If necessary, then the pixel values are weighted and each line may be decided based on the weighted pixel values. Since various methods are known as the method for determining each line, each line may be determined by another method different from the above method.

In the first embodiment, the lines are created in each frame image (Step S6), and the created lines are overlaid on each map (Step S8) to set the lines to the map. However, the lines may be created directly on the map.

In the first embodiment, the unaffected side detection device 601 has the line setting device 602, a line selection device 603 and second overlaying unit 604 to detect the unaffected side. If, however, the unaffected side can be detected, the unaffected side detection device 601 may be configured using another component or constituent element.

Further, in the first embodiment, the display condition determination device 605 has the unaffected side pixel determination unit 74, unaffected-side average value calculation unit 75 and display condition calculation unit 76 to determine the display condition used when each map is displayed. If, however, the display condition used when each map is displayed, can be determined, then the display condition determination device 605 may be configured using another component.

(2) Second Embodiment

Points of difference from the first embodiment will principally be explained upon description of a second embodiment.

Figure 22:
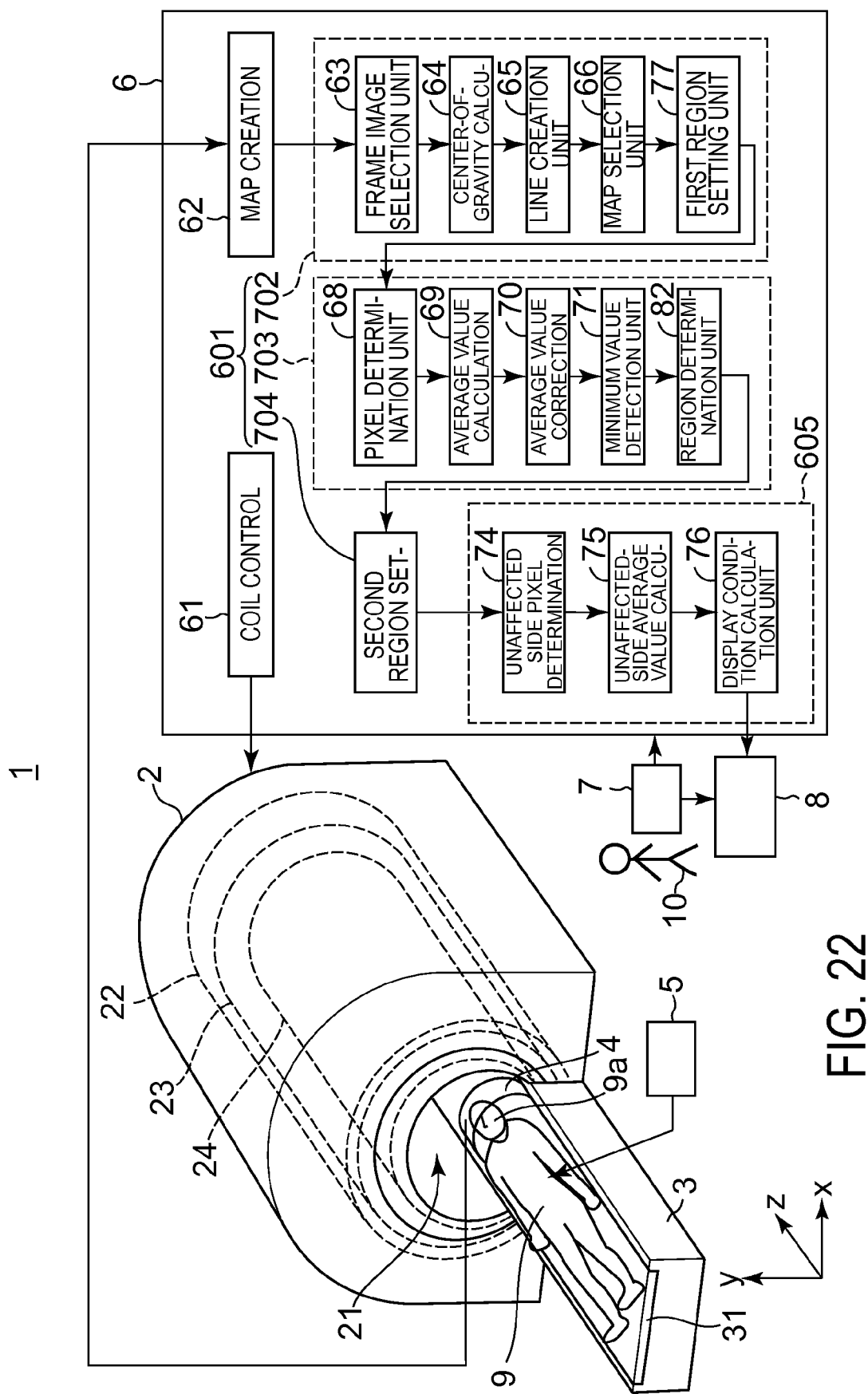
FIG. 22 is a schematic diagram of a second exemplary magnetic resonance imaging system 100.

FIG. 22 is a schematic diagram of a magnetic resonance imaging system 100 according to the second embodiment of the invention.

A controller 6 has a coil control device 61, a map creation device 62, an unaffected side detection device 601 and a display condition determination device 605.

The coil control device 61 and the map creation device 62 are identical to those in the first embodiment.

The unaffected side detection device 601 detects each unaffected side of the subject from each map created by the map creation device 62. The unaffected side detection device 601 has a map division device 702, a region selection device 703 and a second region setting unit 704 to detect each unaffected side.

The map division device 702 divides the map created by the map creation device 62 into a plurality of regions. The map division device 702 has a frame image selection unit 63 through a first region setting unit 77. The frame image selection unit 63, center-of-gravity calculation unit 64, line creation unit 65 and map selection unit 66 are identical to those employed in the first embodiment. The first region setting unit 77 sets a plurality of regions to each map selected by the map selection unit 66.

The region selection device 703 selects a region existing in an unaffected side of a subject 9 from a plurality of regions defined to each map by the map division device 702. The region selection device 703 has a pixel determination unit 68 through a region determination unit 82.

The pixel determination unit 68 determines pixels contained in each region set to the corresponding map.

The average value calculation unit 69 calculates the average values of pixels values of the pixels contained in the respective regions.

The average value correction unit 70 corrects the average values of the pixel values, which have been calculated by the average value calculation unit 69.

The minimum value detection unit 71 detects the minimum value of the average values corrected by the average value correction unit 70.

The region determination unit 82 determines the corresponding region existing in the unaffected side from within the plural regions, based on the minimum value detected by the minimum value detection unit 71.

The second region setting unit 704 sets regions existing in the unaffected side with respect to another map other than the map selected by the map selection unit 66.

The display condition determination device 605 determines a display condition used when each map is displayed, based on the pixel values of pixels existing in the unaffected side in the map. The display condition determination device 605 has an unaffected side pixel determination unit 74 through a display condition calculation unit 76.

The unaffected side pixel determination unit 74 determines pixels contained in each region existing in the unaffected side.

The unaffected-side average value calculation unit 75 calculates the average value of the pixel values of the pixels contained in each region existing in the unaffected side.

The display condition calculation unit 76 calculates a window level WL and a window width WW.

Figure 23:
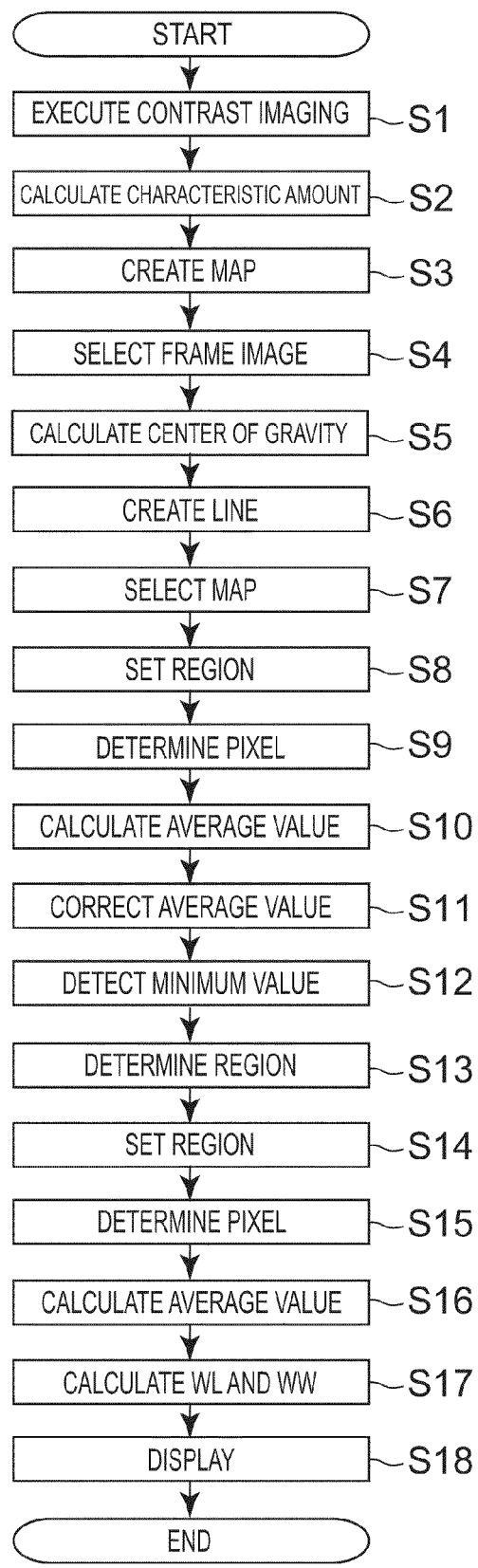
FIG. 23 is a diagram showing a processing flow of the MRI system 100.

FIG. 23 is a diagram showing a processing flow of the MRI system 100.

Since Steps S1 through S7 are similar to those in the first embodiment, their explanations are omitted. After the corresponding map has been selected at Step S7, the processing flow proceeds to Step S8.

At Step S8, the first region setting unit 77 (refer to FIG. 22) overlays lines L1 through L16 and an MTT map of a slice Sk on one another.

Figure 24:
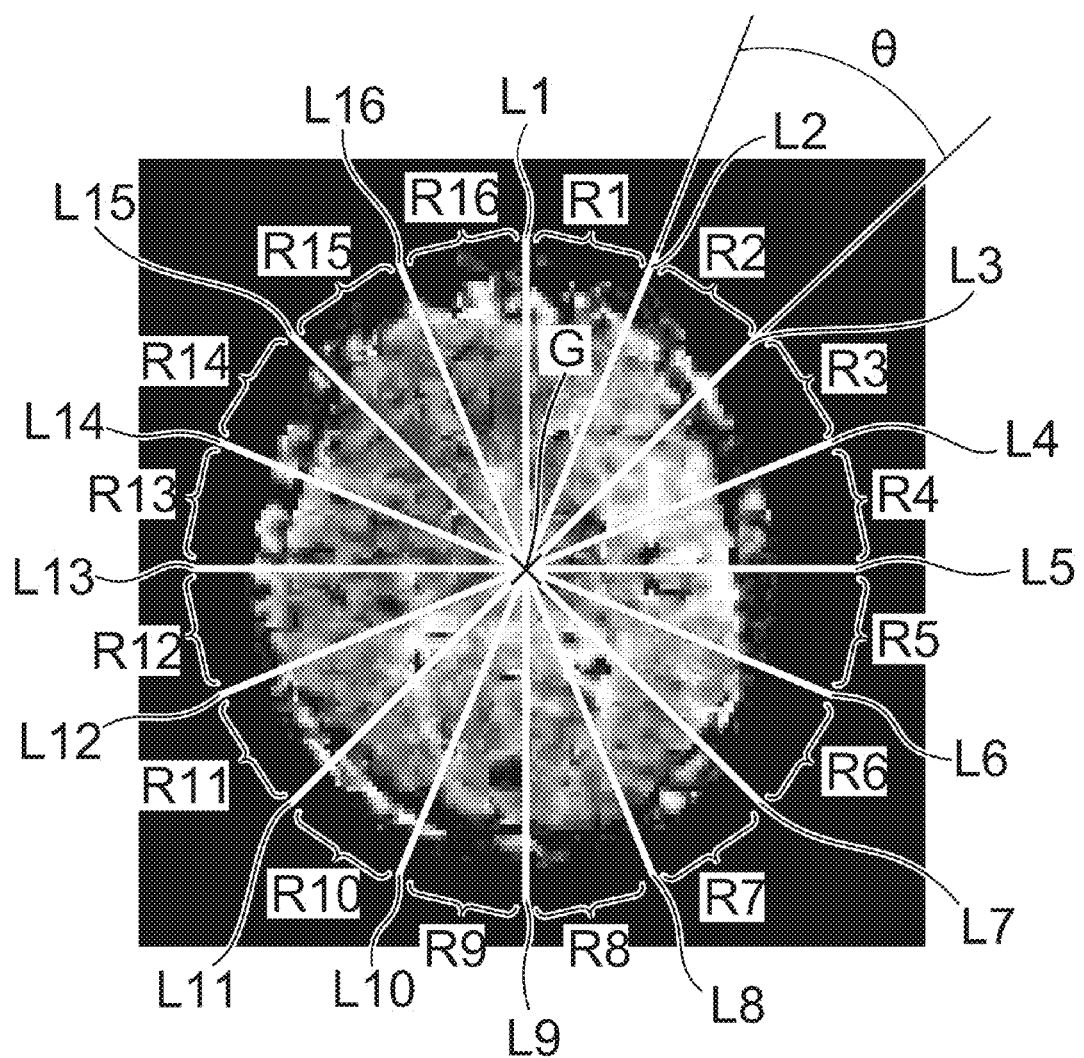
FIG. 24 is a diagram illustrating the manner in which lines L1 through L16 and an MTT map of a slice Sk are overlaid on one another.

FIG. 24 is a diagram showing the manner in which the lines L1 through L16 and the MTT map of the slice Sk are overlaid on one another.

The MTT map is divided into sixteen regions R1 through R16 sandwiched between the adjacent lines by the lines L1 through L16. After the MTT map has been divided into the sixteen regions R1 through R16, the processing flow proceeds to Step S9.

At Step S9, the pixel determination unit 68 (refer to FIG. 22) determines pixels contained in the regions R1 through R16 from within a plurality of pixels held in the MTT map. A description will hereinafter be made of how to determine the pixels contained in the regions R1 through R16.

Figure 25:
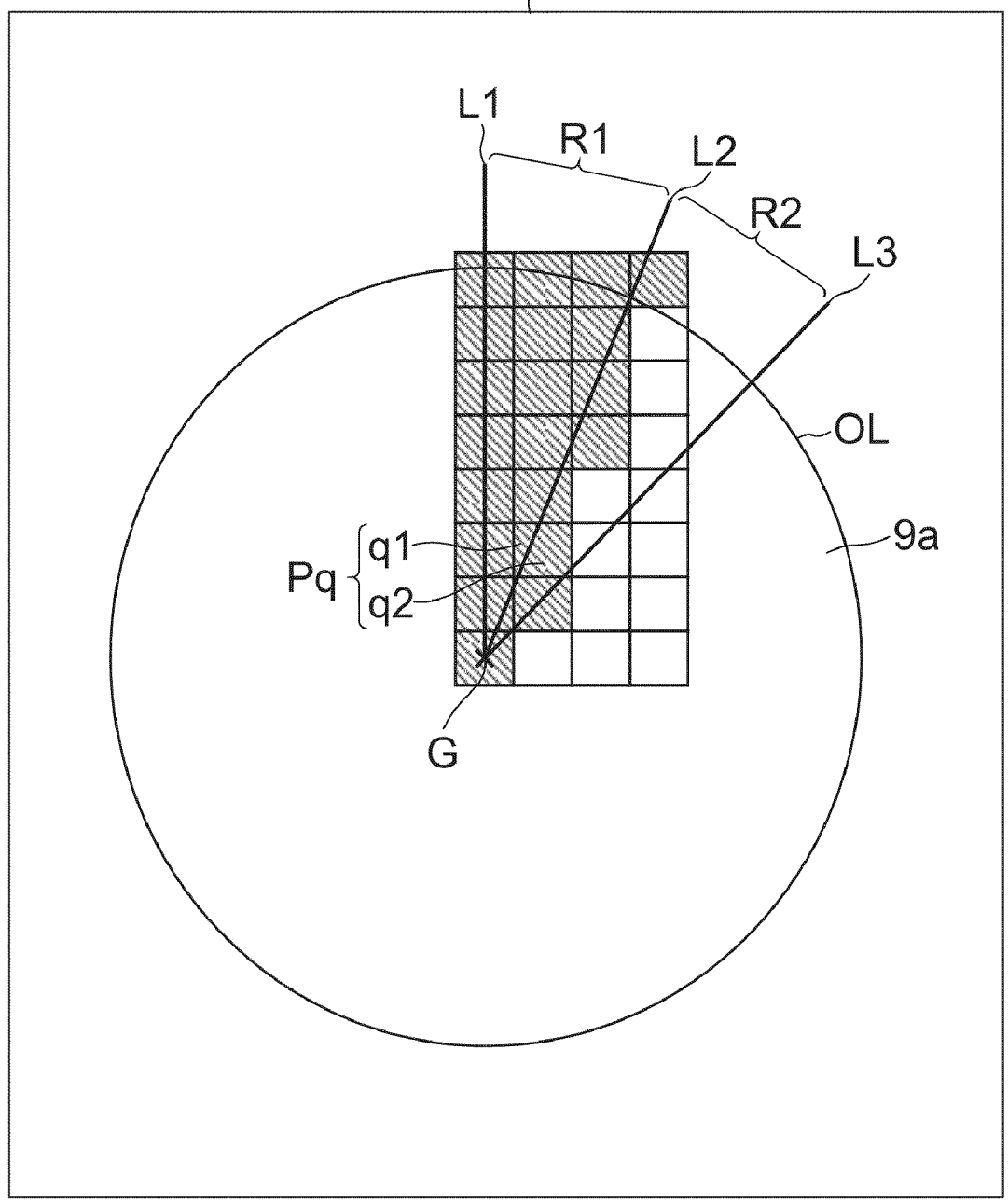
FIG. 25 is a diagram schematically showing regions R1 and R2 in the MTT map.

FIG. 25 is a diagram schematically showing the regions R1 and R2 of the MTT map.

Only the outline OL of the head 9a of the subject 9 is shown in the MTT map of FIG. 25. All pixels in the MTT map are not shown in FIG. 25 and only some pixels existing in the neighborhood of the region R1 are shown in square form. Incidentally, although the size of each pixel is actually made smaller, the pixels are shown on a large scale in FIG. 25 for convenience of explanation.

The pixel determination unit 68 determines pixels sandwiched between the lines L1 and L2 and pixels across which the lines L1 and L2 cut, as the pixels contained in the region R1. In FIG. 25, the determined pixels contained in the region R1 are shown in diagonal lines. Even with respect to the region R2, pixels are determined by the way similar to that for the region R1. Incidentally, pixels sandwiched between the lines L2 and L3 and pixels across which the lines L2 and L3 cut are determined as the pixels contained in the region R2 in the case of the region R2. Accordingly, the pixels across which the line L2 cuts correspond to the pixels contained in the region R1 and the pixels contained in the region R2. Although the pixels contained in the regions R1 and R2 have been explained above, pixels contained in other regions R3 through R16 are explained similarly.

Incidentally, the pixel (pixel Pq, for example) across which the line L2 cuts, corresponds to the pixel contained in the region R1 and is determined to be the pixel contained in the region R2. However, the pixel Pq is divided into a first pixel portion q1 and a second pixel portion q2 by the line L2 as shown in FIG. 25. When the first pixel portion q1 and the second pixel portion q2 are compared with each other, the second pixel portion q2 is larger in area than the first pixel portion q1. Thus, the pixel Pq may be determined to be the pixel contained in the region R2 without being determined as the pixel contained in the region R1. Since various methods are known as the method for determining in which region the pixels are contained, the pixel may be determined by a method different from the above method. After the pixels contained in the regions R1 through R16 have been determined, the processing flow proceeds to Step S10.

At Step S10, the average value calculation unit 69 (refer to FIG. 22) calculates the average values of pixel values of pixels contained in the respective regions for every R1, ..., Rn of regions.

Figure 26:
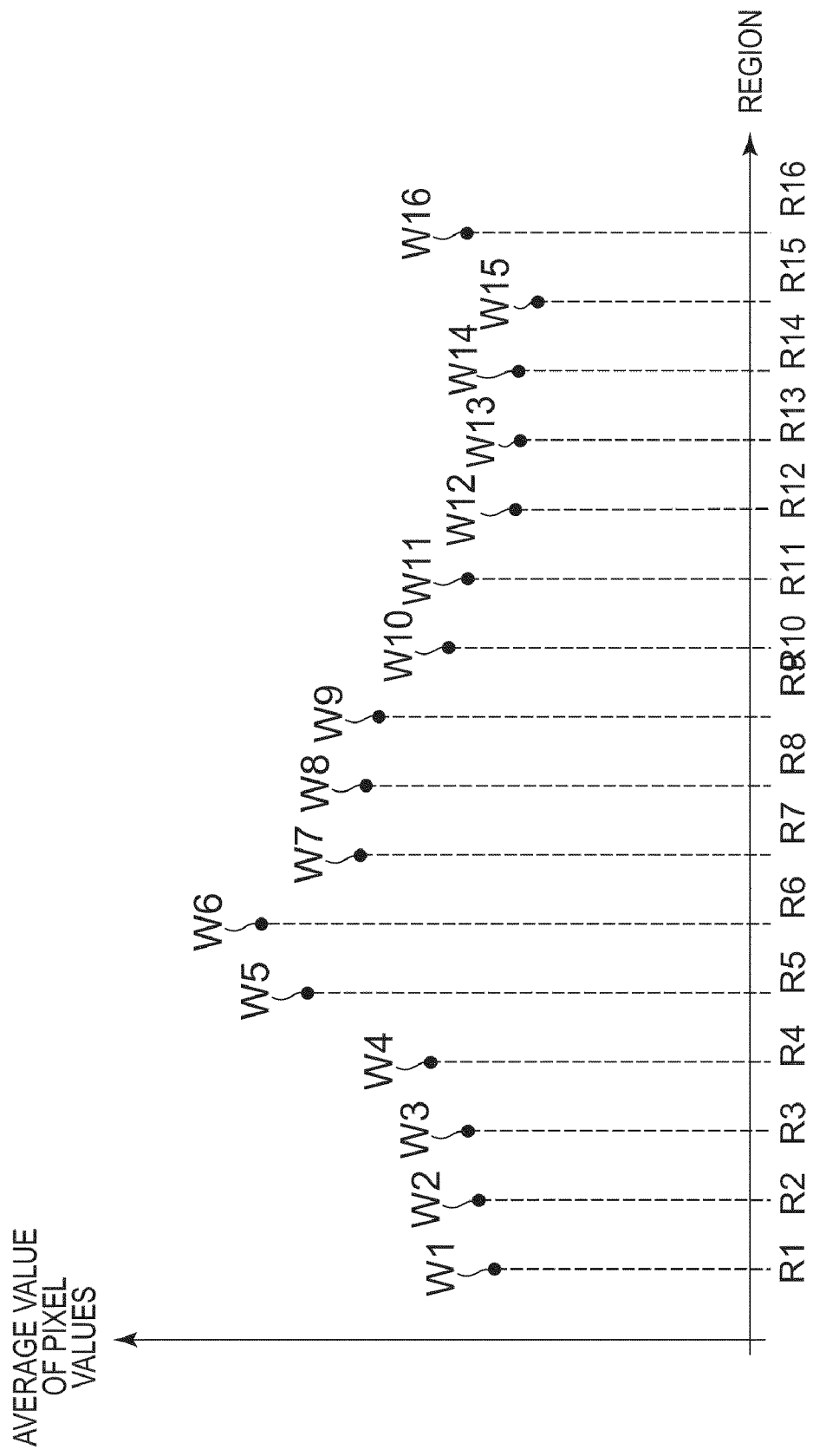
FIG. 26 is a diagram illustrating graphs of average values W1 through W16 of pixel values calculated every region.

FIG. 26 is a diagram showing graphs of average values W1 through W16 of pixel values calculated every region.

The horizontal axis of each graph indicates the region, and the vertical axis thereof indicates the average value of pixel values. Referring to FIG. 26, it is understood that the values of the average values W1 through W16 are different from one another every region. The values of the average values W1 through W16 are values used to determine the regions each existing on the unaffected side of the head of the subject from within the regions R1 through R16 (refer to FIG. 24) at Step S13 to be described later. Increasing each pixel value of the MTT map means that the value of the mean transit time MTT is large as described in the first embodiment. On the other hand, decreasing each pixel value of the MTT map means that the value of the mean transit time MTT is small. Thus, if each region small (i.e., small in the value of the mean transit time MTT) in the average value of pixel values is found out, the corresponding unaffected side can be detected.

Since, however, the average values W1 through W16 of the pixel values are also considered to contain some degree of error respectively, the average values W1 through W16 of the pixel values are corrected in a manner similar to the first embodiment.

Therefore, the processing flow proceeds from Step S10 to Step S11.

At Step S11, the average value correction unit 70 (refer to FIG. 22) corrects the average values W1 through W16 of the pixel values.

Figure 27:
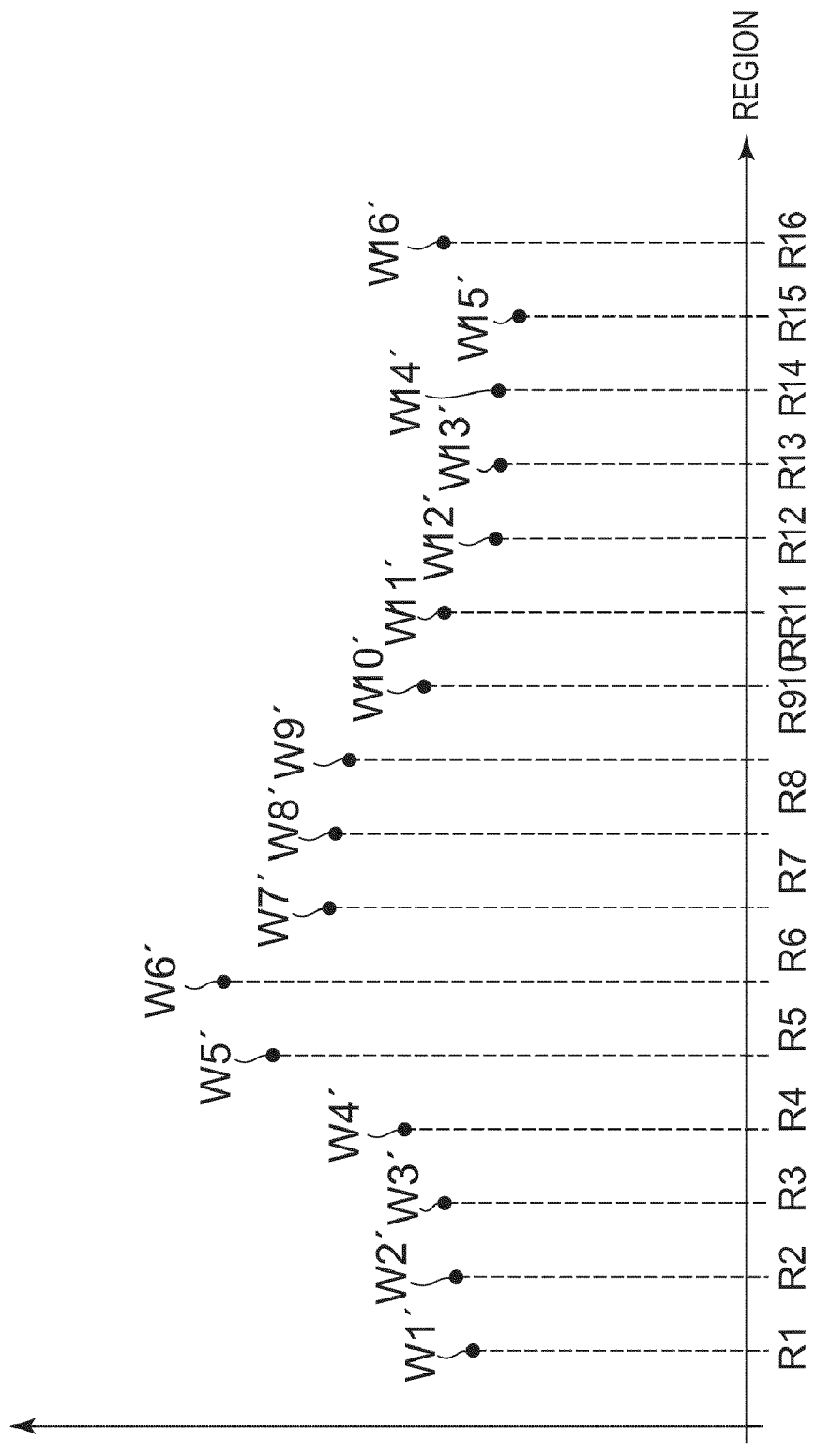
FIG. 27 is a diagram showing one example illustrative of post-correction average values W1' through W16'.

FIG. 27 is a diagram showing one example illustrative of post-correction average values W1' through W16'.

In the second embodiment, the average values W1 through W16 of the pixel values are corrected by a 5-point moving average method to obtain post-correction average values W1' through W16'. For example, the moving average is calculated with respect to the average value W1 of the pixels values using the average value W1 and using the average values lying before and after the average value W1 two by two (average values W15 and W16 and average values W2 and W3). Similarly, the moving average is calculated with respect to the average value W15 of the pixel values using the average value W15 and using the average values lying before and after the average value W15 two by two (average values W13 and W14 and average values W16 and W1). After all the average values W1 through W16 have been corrected by the 5-point moving average method in this way, the processing flow proceeds to Step S12.

At Step S12, the minimum value detection unit 71 (refer to FIG. 22) detects the minimum value out of the post-correction average values W1' through W16'. Since the minimum value is W15' in the second embodiment, the minimum value detection unit 71 detects the average value W15'. After the detection of the average value W15', the processing flow proceeds to Step S13.

At Step S13, the region determination unit 82 (refer to FIG. 22) determines each region existing in the unaffected side from within the regions R1 through R16, based on the post-correction average value W15' detected at Step S12. Since the minimum value W15' of the post-correction average values is obtained by correcting the average value W15 of the region R15, the region R15 is determined to be the region existing on the unaffected side. However, the minimum value W15' is of a value calculated using not only the average value W15 of the pixel values of the region R15 but also the average values W1, W13, W14 and W16 of the pixel values of the regions R1, R13, R14 and R16. Hence, the regions R1, R13, R14 and R16 are also considered to be regions existing on the unaffected side as well as the region R15. Thus, in the second embodiment, the region determination unit 82 determines not only the region R15 but also the regions R1, R13, R14 and R16 as the regions existing on the unaffected side.

Figure 28:
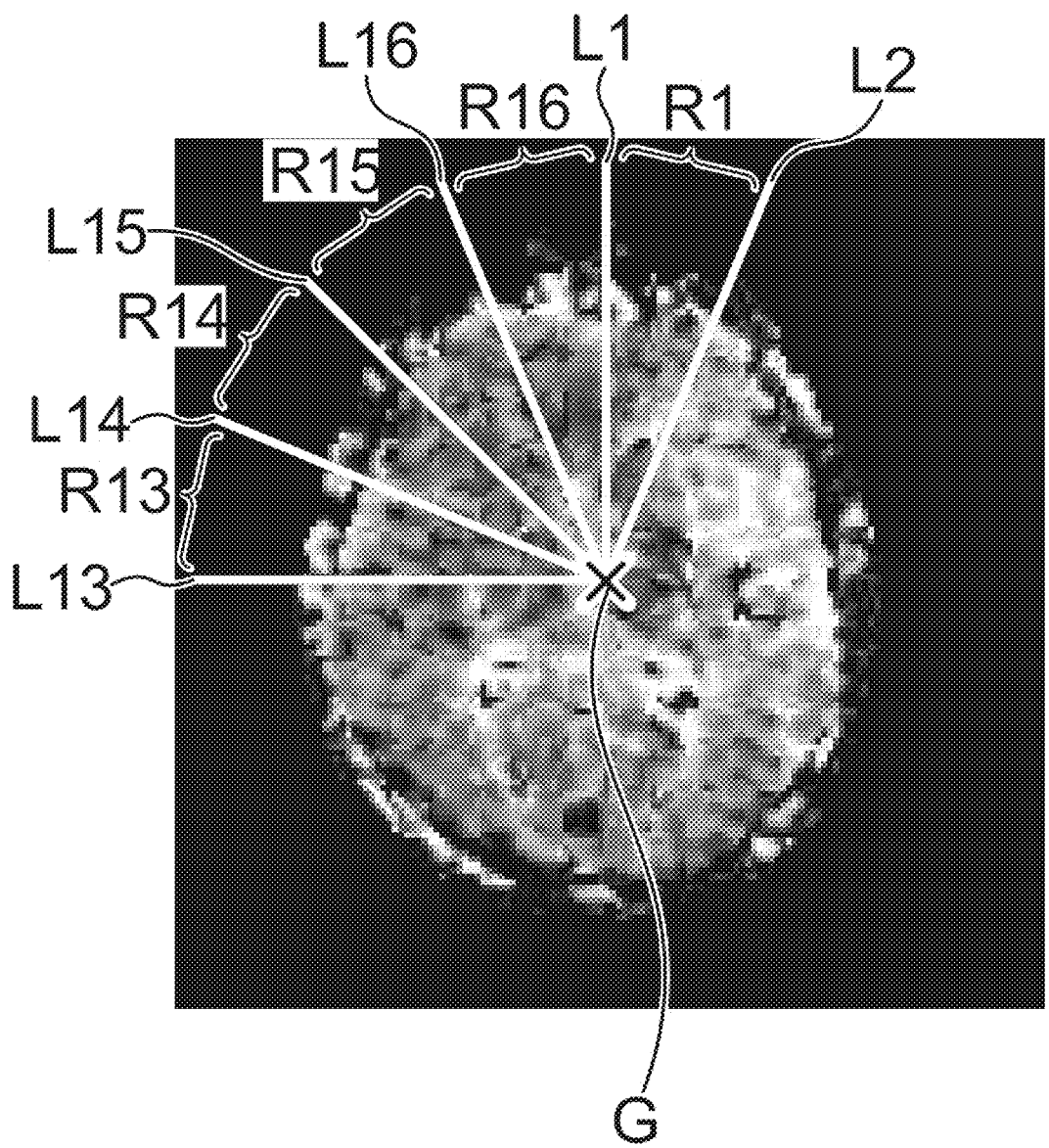
FIG. 28 is a diagram illustrating an MTT map and regions R1 and R13 through R16 existing on the unaffected side.

FIG. 28 is a diagram showing an MTT map (refer to FIG. 24) and regions R1 and R13 through R16 existing on the unaffected side.

The regions R1 and R13 through R16 are located on the upper left side of the MTT map. It is thus understood that at least the upper left side of the head corresponds to the unaffected side. After the regions R1 and R13 through R16 existing on the unaffected side have been determined, the processing flow proceeds to Step S14.

At Step S14, the second region setting unit 704 (refer to FIG. 22) sets the regions R1 and R13 through R16 even to other maps other than the MTT map of the slice Sk and further sets them even to five maps of other slices other than the slice Sk.

Figure 29A:
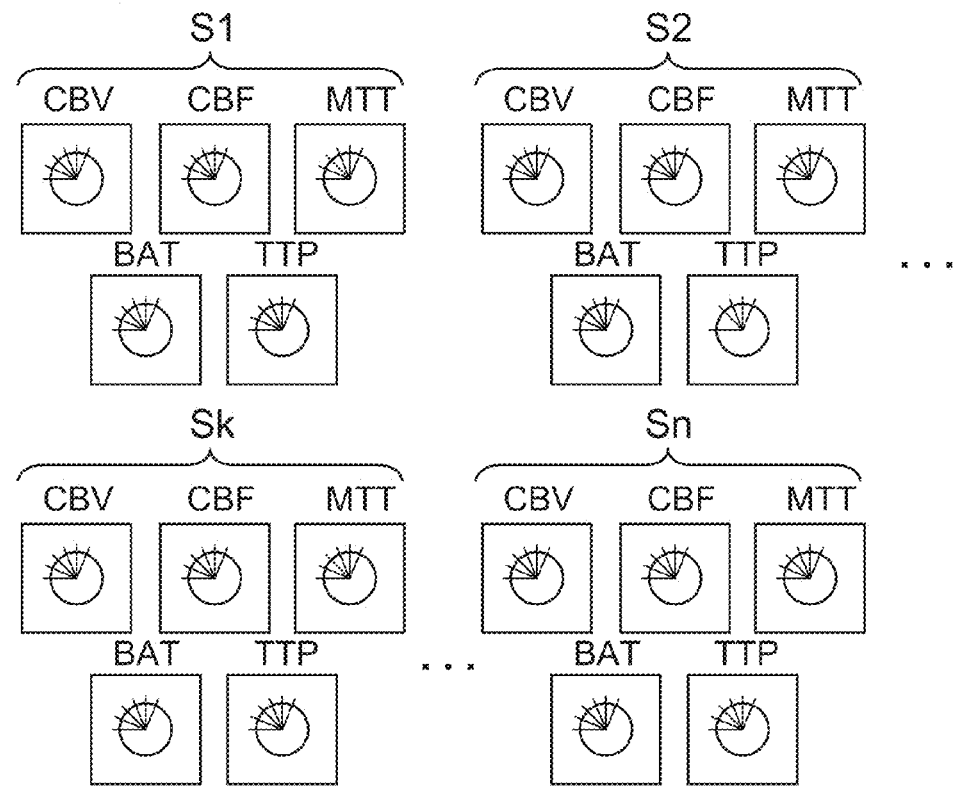
FIGS. 29A and 29B are diagrams showing the manner in which the regions R1 and R13 through R16 are set to their corresponding maps of slices S1 through Sk.
Figure 29B:
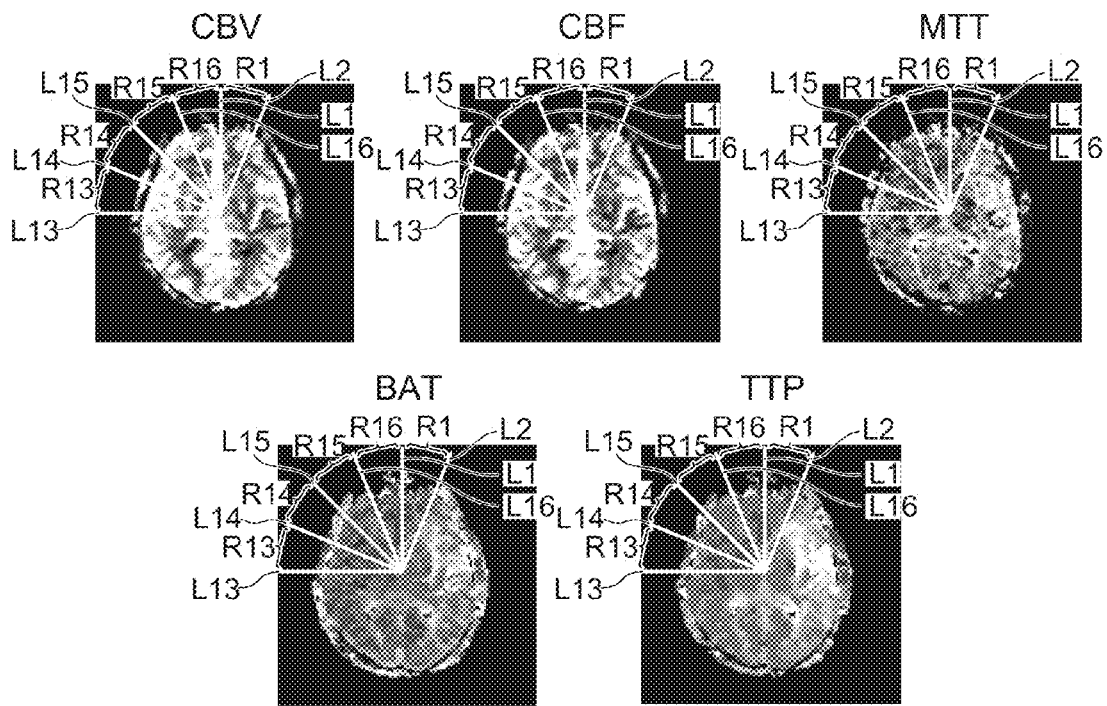

FIGS. 29A and 29B are diagrams showing the manner in which the regions R1 and R13 through R16 are set to their corresponding maps of slices S1 through Sk.

Five maps to which the regions R1 and R13 through R16 are set are schematically shown in FIG. 29A for every S1, . . . , Sn of slices. FIG. 29B shows the five maps of the slice Sk lying in the slices S1 through Sk.

Referring to FIG. 29B, it is understood that the regions R1 and R13 through R16 have been set to the range lying forward on the left side of the head at any map of the slice Sk. While FIG. 29B shows the manner in which the regions R1 and R13 through R16 are set to the five maps of the slice Sk, the regions R1 and R13 through R16 are set to the ranges each lying forward on the left side of the head even at the five maps of other slices.

After the regions R1 and R13 through R16 have been set to all the maps as shown in FIGS. 29A and 29B, the processing flow proceeds to Step S15.

At Step S15, the unaffected side pixel determination unit 74 (refer to FIG. 22) determines pixels contained in the regions R1 and R13 through R16 existing in the unaffected sides with respect to all the maps of slices S1 through Sk. Since the present pixel determining method is identical to the method described while referring to FIG. 25 (Step S9), its description is omitted. After the corresponding pixels have been determined, the processing flow proceeds to Step S16.

At Step S16, the unaffected-side average value calculation unit 75 (refer to FIG. 22) calculates the average values (hereinafter called "unaffected side average values") U of pixel values of pixels existing in unaffected sides every map. The unaffected side average values U are calculated in the following manner.

Since the regions R1 and R13 through R16 correspond to the regions existing in the unaffected sides as described with reference to FIG. 27, the pixels contained in the regions R1 and R13 through R16 result in the pixels that exist in the unaffected sides. Thus, the average values of the pixels contained in the regions R1 and R13 through R16 can be considered to be the average values of the pixel values of the pixels existing in the unaffected sides respectively. Thus, in the second embodiment, the unaffected-side average value calculation unit 75 calculates the average values of the pixels contained in the regions R1 and R13 through R16 as their corresponding unaffected side average values U. For example, the unaffected side average value U is calculated as described below with respect to the MTT map of the slice Sk.

Figure 30:
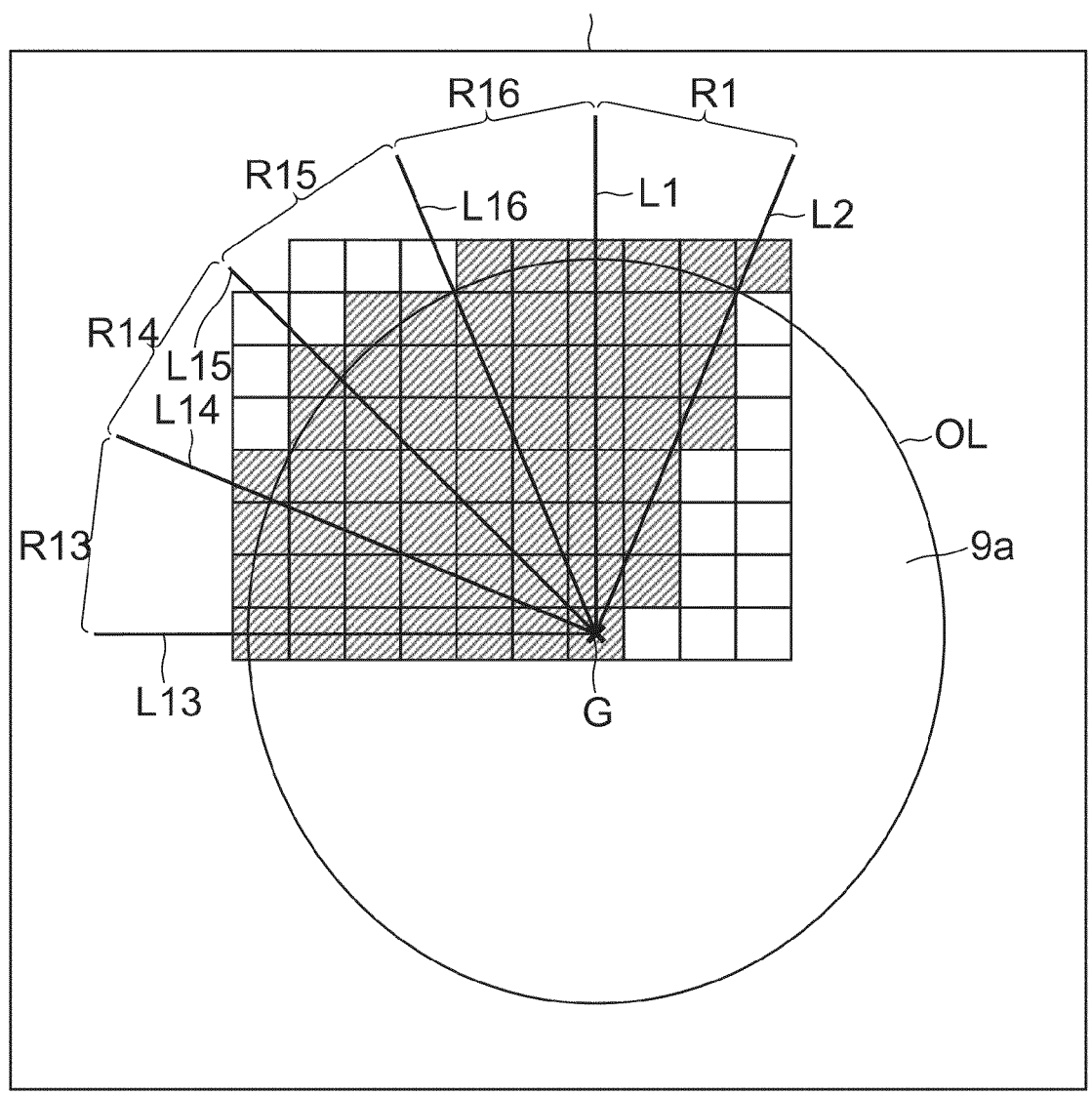
FIG. 30 is an explanatory diagram for calculating an unaffected side average value U in the MTT map of the slice Sk.

FIG. 30 is an explanatory diagram for calculating the unaffected side average value U in the MTT map of the slice Sk.

The pixels determined to be contained in the regions R1 and R13 through R16 are shown in diagonal lines in FIG. 30. The unaffected-side average value calculation unit 75 calculates the average values U of pixels values of all pixels shown in the diagonal lines. Thus, the unaffected-side average value calculation unit 75 calculates the average values of the pixel values of all pixels contained in the regions R1 and R13 through R16 without calculating the average value of the pixel values of the pixels (pixels contained in the region R15, for example) contained in one region. Since the regions R1 and R13 through R16 are considered to be the regions existing in each unaffected side, the unaffected side average value U can be found out by calculating the average value U of the pixel values of all pixels shown in the diagonal lines.

Although the unaffected side average value U of the MTT map for the slice Sk has been described above, the unaffected side average values U of other maps for the slice Sk and the unaffected side average values U of maps for other slices are also similar thereto. The unaffected side average values U are calculated with respect to the maps for all the slices S1 through Sn in the above-described manner. After the calculation of the unaffected side average values U, WL and WW are calculated (Step S17) and the corresponding map is displayed (Step S18).

In the second embodiment, regions existing in an unaffected side are detected. Window levels WL and window widths WW of respective maps are determined based on average values of pixel values of pixels contained in the detected regions. Thus, when an affected or lesion side exists in a subject's imaging range, the unaffected side and the affected side are displayed in different shades of gray. Therefore, images in which unaffected and affected sides are displayed in different shades of gray are automatically displayed with no need to adjust WL and WW by an operator. Therefore, the operator can easily specify an affected side in a short period of time.

Incidentally, although WL and WW have been calculated using the equations (2) and (3) containing the unaffected side average values U in the first and second embodiments (refer to Step S17), WL and WW may be calculated using other equations different from the equations (2) and (3). WL and WW may be calculated by equations using added values of pixels in place of the unaffected side average values U, for example.

In the first and second embodiments, the MTT map has been used to determine the lines L1 and L13 through L16 existing in the unaffected side (refer to FIGS. 17 and 28). Other maps (CBV map, CBF map, BAT map, TTP map, etc.) may however be used.

Many widely different embodiments of the invention may be configured without departing from the spirit and the scope of the present invention. It should be understood that the present invention is not limited to the specific embodiments described in the specification, except as defined in the appended claims.

What is claimed is:

1. A blood flow dynamic analysis apparatus configured to analyze a dynamic state of a blood flow of a subject using data about a plurality of frame images acquired from the subject with a contrast agent injected therein, the blood flow dynamic analysis apparatus comprising:
   a map creation device configured to create a plurality of maps each indicative of a characteristic amount related to the dynamic state of the contrast agent or the blood flow, based on the data about the plurality of frame images;

an unaffected side detection device configured to detect an unaffected side of the subject from within each of the plurality of maps, wherein the unaffected side is free of an anomaly; and a display condition determination device configured to determine a display condition used when each of the plurality of maps is displayed, based on pixel values of pixels existing in the respective unaffected side in each of the plurality of maps.

2. The blood flow dynamic analysis apparatus according to claim 1, wherein the unaffected side detection device comprises:

a line setting device configured to set a plurality of lines to each of the plurality of maps; and a line selection device configured to select each line existing in the unaffected side of the subject from within the plurality of lines set to each of the plurality of maps.

3. The blood flow dynamic analysis apparatus according to claim 2, wherein the line setting device comprises:

a line creation unit configured to create the plurality of lines with respect to each of the plurality of frame images; and a first overlaying unit configured to overlay each of the plurality of maps and the plurality of lines created by the line creation unit.

4. The blood flow dynamic analysis apparatus according to claim 3, wherein the line setting device comprises a frame image selection unit configured to select one frame image from within the plurality of frame images.

5. The blood flow dynamic analysis apparatus according to claim 4, wherein the line creation unit is configured to create the plurality of lines with respect to the frame image selected by the frame image selection unit.

6. The blood flow dynamic analysis apparatus according to claim 5, wherein the line setting device comprises a center-of-gravity calculation unit configured to calculate a center of gravity of the frame image selected by the frame image selection unit.

7. The blood flow dynamic analysis apparatus according to claim 6, wherein the line creation unit is configured to create the plurality of lines extending radially from the center of gravity of the frame image selected by the frame image selection unit.

8. The blood flow dynamic analysis apparatus according to claim 7, wherein the line setting device comprises a map selection unit configured to select each map to which the lines are set.

9. The blood flow dynamic analysis apparatus according to claim 8, wherein the frame image selection unit is configured to select frame images acquired from a first slice of a plurality of slices, and wherein the map selection unit is configured to select a first map created with respect to the first slice from within the plurality of maps.

10. The blood flow dynamic analysis apparatus according to claim 2, wherein the line selection device is configured to calculate pixel values of pixels overlaid on each of plurality of lines for every line set to the map and to select each line existing in the unaffected side of the subject from the plurality of lines, based on the calculated pixel values.

11. The blood flow dynamic analysis apparatus according to claim 10, wherein the line selection device comprises:

a pixel determination unit configured to determine the pixels overlaid on each of the plurality of lines for every line set to the map;

an average value calculation unit configured to calculate the average values of the pixel values of the pixels overlaid on the plurality of lines for every line;

an average value correction unit configured to correct the average values of the pixel values, which are calculated by the average value calculation unit;

a minimum value detection unit configured to detect a minimum value of the average values corrected; and a line determination unit configured to determine each line existing in the unaffected side from within the plurality of lines, based on the minimum value detected.

12. The blood flow dynamic analysis apparatus according to claim 11, wherein the unaffected side detection device comprises a second overlaying unit configured to overlay each line determined by the line determination unit and another map different from the first map.

13. The blood flow dynamic analysis apparatus according to claim 1, wherein the display condition determination device comprises:

an unaffected side pixel determination unit configured to determine pixels overlaid on each line existing in the unaffected side;

an unaffected-side average value calculation unit configured to calculate an average value of pixel values of pixels overlaid on the line existing in the unaffected side; and a display condition calculation unit configured to calculate the display condition used when each of the plurality of maps is displayed, based on the average value calculated by the unaffected-side average calculation unit.

14. The blood flow dynamic analysis apparatus according to claim 1, wherein the unaffected side detection device comprises:

a division device configured to divide each of the plurality of maps into a plurality of regions; and a region selection device configured to select each region existing in the unaffected side of the subject from within the regions.

15. The blood flow dynamic analysis apparatus according to claim 14, wherein a display condition calculation device is configured to calculate the display condition for each of the plurality of maps.

16. The blood flow dynamic analysis apparatus according to claim 1, wherein the display condition is a window level and/or a window width.

17. The blood flow dynamic analysis apparatus according to claim 1, wherein the characteristic amount is at least one of a cerebral blood volume, a cerebral blood flow, a mean transit time, a bolus arrival time, and a time to peak.

18. A magnetic resonance imaging system comprising:

a coil assembly configured to emit at least one pulse;

a reception coil configured to receive a magnetic resonance signal emitted by a subject in response to the at least one emitted pulse;

a controller configured to receive the magnetic resonance signal from the reception coil, the controller further configured to analyze a dynamic state of a blood flow of a subject using data about a plurality of frame images generated using the magnetic resonance signal, the controller comprising:

a map creation device configured to create a plurality of maps each indicative of a characteristic amount related to the dynamic state of contrast agent or the blood flow, based on the data about the plurality of frame images;

an unaffected side detection device configured to detect an unaffected side of the subject from within each of the plurality of maps, wherein the unaffected side is free of an anomaly; and a display condition determination device configured to determine a display condition used when each of the plurality of maps is displayed, based on pixel values of pixels existing in the respective unaffected side in each of the plurality of maps.

19. A program installed in a controller of a blood flow dynamic analysis apparatus for use in analyzing a dynamic state of a blood flow of a subject using data about a plurality of frame images acquired from the subject with a contrast agent injected therein, the program including instructions configured to cause the blood flow dynamic analysis apparatus to function as:

a map creation device for creating maps each indicative of a characteristic amount related to the dynamic state of the contrast agent or the blood flow, based on the data about the plurality of frame images;

an unaffected side detection device for detecting an unaffected side of the subject from within each of the plurality of maps, wherein the unaffected side is free of an anomaly; and a display condition determination device for determining a display condition used when each of the maps is displayed, based on pixel values of pixels existing in the respective unaffected side in each of the plurality of maps.

* * * * *